United States Patent
Meyer et al.

(10) Patent No.: US 6,312,958 B1
(45) Date of Patent: Nov. 6, 2001

(54) METHOD FOR MARKING LIQUIDS WITH AT LEAST TWO MARKER SUBSTANCES AND METHOD FOR DETECTING THEM

(75) Inventors: Frank Meyer, Heidelberg; Gerhard Wagenblast, Wachenheim; Karin Heidrun Beck, Ludwigshafen; Christos Vamvakaris, Kallstadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/673,736
(22) PCT Filed: Apr. 12, 1999
(86) PCT No.: PCT/EP99/02451
  § 371 Date: Oct. 20, 2000
  § 102(e) Date: Oct. 20, 2000
(87) PCT Pub. No.: WO99/56125
  PCT Pub. Date: Nov. 4, 1999

(30) Foreign Application Priority Data

Apr. 23, 1919 (DE) ................................. 198 18 176

(51) Int. Cl.⁷ ..................................... G01N 21/17
(52) U.S. Cl. ................... 436/56; 436/27; 436/29; 436/139; 436/172
(58) Field of Search .................. 436/56, 27, 29, 436/139, 172; 44/300; 585/14

(56) References Cited

U.S. PATENT DOCUMENTS

| | | |
|---|---|---|
| 3,023,186 | 2/1962 | Geiger . |
| 3,484,467 | 12/1969 | Susi et al. . |
| 4,806,664 | 2/1989 | Schrott et al. . |
| 5,047,312 | 9/1991 | Albert et al. . |
| 5,061,596 | 10/1991 | Albert et al. . |
| 5,084,592 | 1/1992 | W. Schrott et al. . |
| 5,512,066 * | 4/1996 | Toman et al. ............ 44/300 |
| 5,703,229 | 12/1997 | Krutak et al. . |
| 5,804,447 | 9/1998 | Albert et al. . |
| 5,843,783 * | 12/1998 | Rutledge et al. ......... 436/56 |
| 5,958,780 * | 9/1999 | Asher et al. ............. 436/56 |
| 5,981,283 * | 10/1999 | Anderson et al. ......... 436/27 |
| 6,003,365 * | 12/1999 | Pope et al. ............. 73/152.39 |

FOREIGN PATENT DOCUMENTS

| | | |
|---|---|---|
| 1 073 739 | 9/1994 | (DE) . |
| 0 155 780 | 9/1985 | (EP) . |
| 0 192 215 | 4/1988 | (EP) . |
| 0 336 213 | 10/1989 | (EP) . |
| 0 358 080 | 3/1990 | (EP) . |
| 0 310 080 | 5/1990 | (EP) . |
| 0 464 543 | 1/1992 | (EP) . |
| 2 168 372 | 6/1986 | (GB) . |
| 2 200 650 | 8/1988 | (GB) . |
| WO 94/02570 | 2/1994 | (WO) . |

OTHER PUBLICATIONS

F.H. Moser, et al., vol. II, pp. 3–13, "The Phthalocyanines," 1983.

B.L. Wheeler, et al., J. Am. Chem. Soc., vol. 106, pp. 7404–7410, "A Silicon Phthalocyanine and a Silicon Naphthalocyanine: Synthesis, Electrochemistry, and Electrogenerated Chemiluminscence;" 1984.

* cited by examiner

*Primary Examiner*—Jill Warden
*Assistant Examiner*—Yelena G. Gakh
(74) *Attorney, Agent, or Firm*—Oblon, Spivak, McClelland, Maier & Neustadt, P.C.

(57) ABSTRACT

The present invention relates to a method of marking liquids using at least two markers, wherein said markers absorb in the 600–1200 nm region of the spectrum and reemit fluorescent light and the absorption range of at least one marker overlaps with the absorption range of at least one other marker.

The present invention further relates to a method for detecting markers in liquids marked by the method of the invention, which comprises using light sources which emit radiation in the absorption ranges of said markers and detecting the fluorescent light reemitted by said markers, at least one of said light sources emitting radiation in the overlapping absorption range of at least one marker with that of at least one other marker and the number of light sources being less than or equal to the number of markers.

The present invention further relates to liquids marked by the method of the invention.

9 Claims, No Drawings

METHOD FOR MARKING LIQUIDS WITH AT LEAST TWO MARKER SUBSTANCES AND METHOD FOR DETECTING THEM

BACKGROUND OF THE INVENTION

1. Field of the Invention

The present invention relates to a method of marking liquids using at least two markers, wherein said markers absorb in the 600–1200 nm region of the spectrum and reemit fluorescent light and the absorption range of at least one marker overlaps with the absorption range of at least one other marker.

2. Description of the Related Art

The present invention further relates to a method for detecting markers in liquids marked by the method of the invention, which comprises using light sources which emit radiation in the absorption ranges of said markers and detecting the fluorescent light reemitted by said markers, at least one of said light sources emitting radiation in the overlapping absorption range of at least one marker with that of at least one other marker and the number of light sources being less than or equal to the number of markers.

The present invention further relates to liquids marked by the method of the invention.

It is frequently necessary to mark, or tag, liquids to allow their subsequent detection, for example in use, by means of suitable methods. This makes it possible, for example, to differentiate heating oil, which normally enjoys a favorable tax status, from the generally more highly taxed diesel oil, or to tag liquid product streams in large industrial plants, for example petroleum refineries, and to trace them thereby.

If the marking of the liquids is to be invisible to the human eye, it is necessary to resort to the use of markers which absorb and/or emit radiation outside the visible region of the spectrum. Owing to the extreme sensitivity of detection and the attendant possibility of achieving reliable marking with low levels of added marker, pride of place belongs here especially to markers which reemit the absorbed radiation as fluorescent light. This emitted radiation generally has a lower frequency than the absorbed radiation (STOKES radiation), less frequently the same frequency (resonance fluorescence) or even a higher frequency (ANTI-STOKES radiation).

Great economic importance attaches to the marking of hydrocarbons and hydrocarbon mixtures (e.g., various grades of diesel and gasoline motor fuels and of other mineral oils). Since these liquids usually themselves have high absorption and/or fluorescence in the region of the spectrum below about 600 nm, its is not surprising that the markers used absorb and/or fluoresce above about 600 nm.

Ideally, compounds useful as markers should therefore possess the following basic properties:

strong absorption in the 600–1200 nm region of the spectrum, little or no absorption/fluorescence in the visible region of the spectrum, strong emission of fluorescent light in the region of the spectrum which extends from about 600 to about 1200 nm, give detectable emission levels of fluorescence when added to the liquid in question at less than 1 ppm by weight, and adequate solubility in the liquid to be marked.

In addition, depending on the specific application requirements, compounds useful as markers may have to satisfy one or more of the following requirements:

miscibility with other markers and any other additives present (the marked and possibly additived liquids should also be miscible with each other), adequate stability to the action of external conditions, e.g., temperature, light, moisture, etc., alone and dissolved in the liquid to be marked, not be harmful to the environment in which they are used, e.g., internal combustion engines, storage tanks, etc., and be both toxicologically and ecologically safe.

WO 94/02570 describes marking liquids by using markers having their absorption maximum within the range from 600 to 1200 nm and/or a fluorescence maximum within the range from 620 to 1200 nm selected from the group consisting of the metal-free and metal-containing phthalocyanines, the metal-free and metal-containing naphthalocyanines, the nickel-dithiolene complexes, the aminium compounds of aromatic amines, the methine dyes and the azulenesquaric acid dyes. It further describes a method essentially comprising detecting the fluorescent light of the marker present in the liquid, which marker absorbs radiation in the stated region of the spectrum. The cited reference also describes a detector for the marker. However, the simultaneous use of two or more markers is not explicitly mentioned.

U.S. Pat. No. 5,525,516 likewise describes a method for marking mineral oils with compounds which fluoresce in the NIR region. Substituted phthalocyanines, substituted naphthalocyanines and squaric or croconic acid derivatives are used as such markers. This U.S. Patent states in the description part (column 3, lines 35 to 40) that it is also within the scope of the invention described therein to mark one or more mineral oils not just with one, but also with two or more compounds which fluoresce in the IR region. It is further stated in this passage that these two or more compounds are selected so that they absorb IR radiation and/or reemit fluorescent light at wavelengths different enough from each other so as not to interfere with individual detection. Using the (then) state of the art detection equipment it is believed (column 4, lines 25 to 28) that such differences in absorption/fluorescence of as little as 20 nm in wavelength can be discerned. This reference explicitly rules out using markers having overlapping regions of absorption. What is more, it is pointed out (column 3, lines 41 to 44) that this or these fluorescent compound(s) should preferably absorb at wavelengths below 850 nm, since mineral oils absorb above this wavelength.

U.S. Pat. No. 5,525,516 further claims a method for identifying mineral oils which have been marked with one or more markers. The marked mineral oil, or the markers incorporated therein, are exposed to electromagnetic radiation within the range (absorption range) of 670–850 nm. But beyond that no further information is provided as to how to proceed when mineral oils have been marked with more than one marker.

U.S. Pat. No. 5,710,046 describes a method for tagging gasoline, again essentially by detecting an essentially metal-free fluorescent dye dissolved in the gasoline. An appropriately tagged gasoline is excited with radiation from a wavelength band of 600 to 2500 nm, the fluorescent light emitted by the dye in the wavelength band from about 600 to 2500 nm is detected, and the resulting detection signal is used to identify the tagged sample. This reference further describes at length the construction of a detector for detecting the fluorescent dyes in the tagged gasoline samples. However, the use of a plurality of markers (dyes) is not discussed.

If liquids, for example hydrocarbons and hydrocarbon mixtures (e.g., diesel and gasoline fuels and other mineral oils), from different sources or different manufacturers are to be marked, a multiplicity of different markers are required if only one marker is used per liquid. These different markers have to be sufficiently different in their absorption and/or fluorescence characteristics in order that the liquids may be identified with regard to their provenience and/or producer. Moreover, marking liquids with just one marker makes it easier for others to falsify unmarked liquids by adding the appropriate marker. This is of immense significance when chemically and qualitatively equivalent liquids carry different fiscal duties. An example are heating oil and diesel fuel.

BRIEF SUMMARY OF THE INVENTION

It is an object of the present invention to use two or more markers to mark liquids with a "fingerprint" signature which is difficult to reproduce.

We have found that this object is achieved by a method of marking liquids using at least two markers, wherein
said markers absorb in the 600–1200 nm region of the spectrum and reemit fluorescent light and
the absorption range of at least one marker overlaps with the absorption range of at least one other marker.

Preferably, markers are used whose respective maximum absorption wavelength is in the 600–1200 nm region of the spectrum.

DETAILED DESCRIPTION OF THE INVENTION

The use of two or more markers having an overlap between the absorption range of at least one marker and the absorption range of at least one further marker makes it possible, on the one hand, to use a larger number of markers within the wavelength range mentioned. More importantly, however, any compounds used by others in an attempt at fraudulent misrepresentation need to have not just similar absorption maxima to the original markers, but also similar characteristics to the latter in the rest of the absorption range as well.

Let it be assumed, for example, that each fraudulent marker has only one, relatively narrow absorption maximum which corresponds to that of an original marker. Let it be further assumed that the original markers additionally have absorption ranges which overlap to some extent, i.e., that marking in the sense of the present invention has been effected. If, then, light sources are used which emit only in the regions of the absorption maxima, similar fluorescence spectra are likely in the two cases. If, however, light sources are used which emit at wavelengths at which the fraudulent markers have no absorption, but the original markers have overlapping absorption ranges, then fluorescent light emitted by these markers would be expected to be detected in the latter case but not in the former case.

Another example. Let it be assumed that the absorption maximum of an original marker M1 is located in the absorption region of another original marker M2. If M1 and M2 are each excited in their absorption maximum, then the flourescent signal of M1 will be due only to its excitation, whereas the flourescent signal of marker M2 will have a component due to its individual excitation (in the absorption maximum of M2) and the other component, which is due to the excitation of marker M1 (in its absorption maximum and simultaneously in the region of absorption overlap between markers M1 and M2). In contra-distinction thereto, corresponding fraudulent markers without absorption ranges overlapping in such a way will on excitation in their absorption maxima exhibit only their respective, individual flourescent signals. This will be discussed in greater detail later in this text.

Preference is given in the method of the invention for marking liquids to using a combination of n markers, where n is an integer from 2 to 10, i.e., 2, 3, 4, 5, 6, 7, 8, 9 or 10.

Particular preference is given in the method of the invention for marking liquids to using a combination of n markers, where n is an integer from 2 to 6, i.e., 2, 3, 4, 5 or 6.

Very particular preference is given in the method of the invention for marking liquids to using a combination of n markers, where n is an integer from 2 to 4, i.e., 2, 3 or 4.

Preferred markers added in the method of the invention and also in the preferred embodiments in which a combination of n=2–10, n=2–6 or n=2–4, markers is used, are compounds selected from the group consisting of metal-free and metal-containing phthalocyanines, metal-free and metal-containing naphthalocyanines, nickel-dithiolene complexes, aminium compounds of aromatic amines, methine dyes, squaric acid dyes and croconic acid dyes.

Suitable phthalocyanines conform for example to the formula Ia

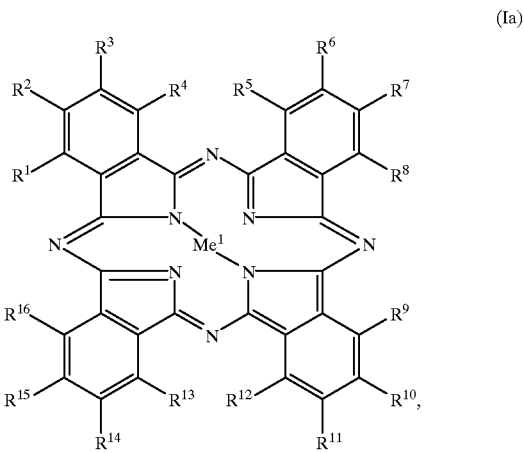

(Ia)

where
Me$^1$ is two hydrogens, two lithiums, magnesium, zinc, copper, nickel, VO, TiO, AlCl, AlO—$C_1$–$C_{20}$-alkyl, AlNH—$C_1$–$C_{20}$-alkyl, AlN($C_1$–$C_{20}$-alkyl)$_2$, AlO—$C_6$–$C_{20}$-aryl, Al—NH—$C_6$–$C_{20}$-aryl or AlN($C_6$–$C_{20}$-aryl)$_2$, AlN—Het, where N—Het is a heterocyclic, saturated or unsaturated five-, six- or seven-membered ring which, as well as at least one nitrogen atom, can contain one or two further nitrogen atoms and/or a further oxygen or sulfur atom in the ring, which is unsubstituted or singly to triply substituted by $C_1$–$C_4$-alkyl, phenyl, benzyl or phenylethyl and which is attached to the aluminum atom via a (or the) ring nitrogen atom, or Si(OH)$_2$,
at least 4 of the radicals R$^1$ to R$^{16}$ are each independently a radical of the formula W—X$^1$, where W is a chemical bond, oxygen, sulfur, imino, $C_1$–$C_4$-alkylimino or phenylimino and X$^1$ is $C_1$–$C_{20}$-alkyl or $C_3$–$C_{10}$-cycloalkyl with or without interruption by from 1 to 4 oxygen atoms in ether function and with or without phenyl substitution, adamantyl or substituted or unsubstituted phenyl, heterocyclic, saturated five-, six- or seven-membered rings which can additionally contain one or two further nitrogen atoms and/or one further oxygen or sulfur atom in the ring, which are unsubstituted or singly to triply substituted by $C_1$–$C_4$-alkyl, phenyl, benzyl or phenylethyl and which are attached to the benzene ring via a (or the) ring nitrogen atom, and any remaining radicals $R^1$ to $R^{16}$ are each hydrogen, halogen, hydroxysulfonyl or $C_1$–$C_4$-dialkylsulfamoyl.

Suitable phthalocyanines further conform for example to the formula Ib

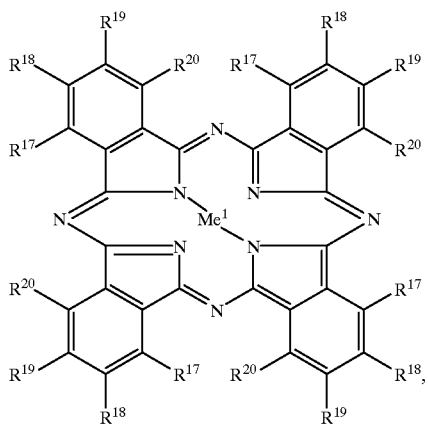

where $R^{17}$ and $R^{18}$ or $R^{18}$ and $R^{19}$ or $R^{19}$ and $R^{20}$ are paired off to form a radical of the formula $X^2$—$C_2H_4$—$X^3$, where one of $X^2$ and $X^3$ is oxygen and the other is imino or $C_1$–$C_4$-alkylimino, and $R^{19}$ and $R^{20}$ or $R^{17}$ and $R^{20}$ or $R^{17}$ and $R^{18}$ are each independently hydrogen or halogen, and $Me^1$ is as defined above.

Further suitable phthalocyanines, unless already mentioned among the above-recited phthalocyanines, are shown in U.S. Pat. No. 5,526,516 under the general formula I and exemplarily in Table 3 and also in U.S. Pat. No. 5,703,229 under the general formula II and exemplarily in Table 3.

Suitable naphthalocyanines conform for example to the formula II

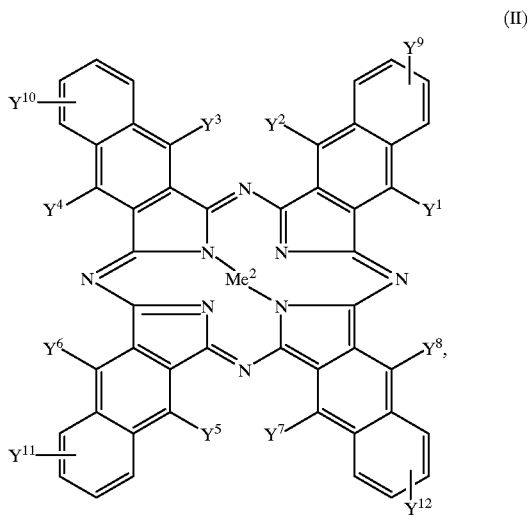

where $Y^1, Y^2, Y^3, Y^4, Y^5, Y^6, Y^7$ and $Y^8$ are each independently hydrogen, hydroxyl, $C_1$–$C_{20}$-alkyl, $C_3$–$C_{10}$-cycloalkyl or $C_1$–$C_{20}$-alkoxy, where the alkyl groups may each be interrupted by from 1 to 4 oxygen atoms in ether function and may be phenyl-substituted, heterocyclic, saturated five-, six- or seven-membered rings which can additionally contain one or two further nitrogen atoms and/or a further oxygen or sulfur atom in the ring, which are unsubstituted or singly to triply substituted by $C_1$–$C_4$-alkyl, phenyl, benzyl or phenylethyl and which are attached to the benzene ring via a (or the) ring nitrogen atom, $Y^9, Y^{10}, Y^{11}$ and $Y^{12}$ are each independently hydrogen, $C_1$–$C_{20}$-alkyl or $C_1$–$C_{20}$-alkoxy, where the alkyl groups may each be interrupted by from 1 to 4 oxygen atoms in ether function, halogen, hydroxysulfonyl or $C_1$–$C_4$-dialkylsulfamoyl, and $Me^2$ is $Me^1$ or is the radical

where $Y^{17}$ and $Y^{18}$ are each independently hydroxyl, $C_1$–$C_{20}$-alkoxy, $C_1$–$C_{20}$-alkyl, $C_2$–$C_{20}$-alkenyl, $C_3$–$C_{20}$-alkenyloxy or a radical of the formula

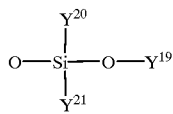

where $Y^{19}$ is $C_1$–$C_{20}$-alkyl, $C_2$–$C_{20}$-alkenyl or $C_4$–$C_{20}$-alkadienyl and $Y^{20}$ and $Y^{21}$ are each independently $C_1$–$C_{12}$-alkyl, $C_2$–$C_{12}$-alkenyl or the abovementioned radical $OY^{19}$.

Of particular interest in this connection are naphthalocyanines of the formula II in which at least one of the radicals $Y^1$ to $Y^8$ is not hydrogen.

Further suitable naphthalocyanines, unless already mentioned among the above-recited naphthalocyanines, are shown in U.S. Pat. No. 5,526,516 under the general formula II and exemplarily in Table 4 and also in U.S. Pat. No. 5,703,229 under the general formula III and exemplarily in Table 4.

Suitable nickel-dithiolene complexes conform for example to the formula III

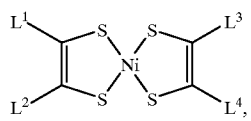

(III)

where $L^1$, $L^2$, $L^3$ and $L^4$ are each independently $C_1$–$C_{20}$-alkyl, with or without interruption by from 1 to 4 oxygen atoms in ether function, phenyl, $C_1$–$C_{20}$-alkylphenyl, $C_1$–$C_{20}$-alkoxyphenyl, where the alkyl groups may each be interrupted by from 1 to 4 oxygen atoms in ether function, or $L^1$ and $L^2$ and/or $L^3$ and $L^4$ are in each case together the radical of the formula

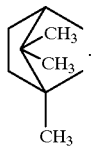

Suitable aminium compounds conform for example to the formula IV

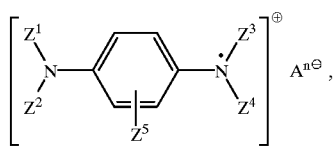

(IV)

where $Z^1$, $Z^2$, $Z^3$ and $Z^4$ are each independently $C_1$–$C_{20}$-alkyl, with or without interruption by from 1 to 4 oxygen atoms in ether function, $C_1$–$C_{20}$-alkanoyl or a radical of the formula

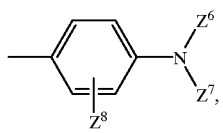

where $Z^6$ is hydrogen, $C_1$–$C_{20}$-alkyl with or without interruption by from 1 to 4 oxygen atoms in ether function, or $C_1$–$C_{20}$-alkanoyl, $Z^7$ is hydrogen or $C_1$–$C_{20}$-alkyl with or without interruption by from 1 to 4 oxygen atoms in ether function, and $Z^8$ is hydrogen, $C_1$–$C_{20}$-alkyl with or without interruption by from 1 to 4 oxygen atoms in ether function or halogen, and $A^{n\ominus}$ is the equivalent of an anion.

Suitable methine dyes conform for example to the formula V

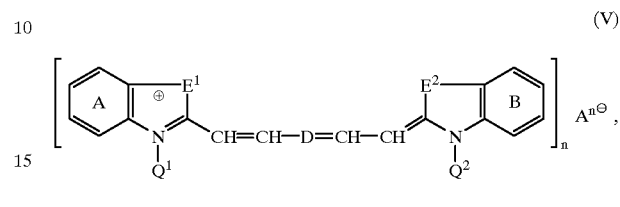

(V)

where the rings A and B may each be independently benzofused and substituted, $E^1$ and $E^2$ are each independently oxygen, sulfur, imino or a radical of the formula —C(CH$_3$)$_2$— or —CH=CH—, D is a radical of the formula

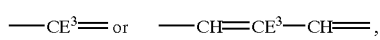

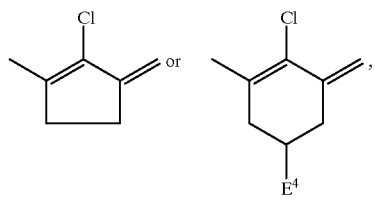

where $E^3$ is hydrogen, $C_1$–$C_6$-alkyl, chlorine or bromine and $E^4$ is hydrogen or $C_1$–$C_6$-alkyl, $Q^1$ and $Q^2$ are each independently phenyl, $C_5$–$C_7$-cycloalkyl, $C_1$–$C_{12}$-alkyl with or without interruption by from 1 to 3 oxygen atoms in ether function and with or without substitution by hydroxyl, chlorine, bromine, carboxyl, $C_1$–$C_4$-alkoxycarbonyl, acryloyloxy, methacryloyloxy, hydroxysulfonyl, $C_1$–$C_7$-alkanoylamino, $C_1$–$C_6$-alkylcarbamoyl, $C_1$–$C_6$-alkylcarbamoyloxy or a radical of the formula $G^{\oplus}(K)_3$, where G is nitrogen or phosphorus and K is phenyl, $C_5$–$C_7$-cycloalkyl or $C_1$–$C_{12}$-alkyl, $A^{n\ominus}$ is the equivalent of an anion, and n is 1, 2 or 3.

Suitable squaric acid dyes are for example those compounds which are shown in U.S. Pat. No. 5,526,516 under the general formula III and exemplarily in Table 2 and are recited in U.S. Pat. No. 5,703,229 under the general formula IV and exemplarily in Table 2.

Suitable squaric acid dyes also include azulenesquaric acid dyes which conform for example to the below-indicate formula VI

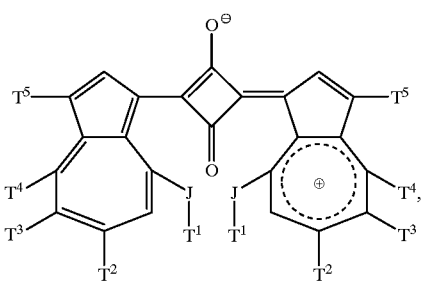

(VI)

where
J is $C_1$–$C_{12}$-alkylene,
$T^1$ is hydrogen, halogen, amino, hydroxyl, $C_1$–$C_{12}$-alkoxy, phenyl, substituted phenyl, carboxyl, $C_1C_{12}$-alkoxycarbonyl, cyano or a radical of the formula —$NT^7$—CO—$T^6$, —CO—$NT^6T^7$ or O—CO—$NT^6T^7$, where $T^6$ and $T^7$ are each independently hydrogen, $C_1$–$C_{12}$-alkyl, $C_5$–$C_7$-cycloalkyl, phenyl, 2,2,6,6-tetramethylpiperidin-4-yl or cyclohexylaminocarbonyl, and
$T^2$, $T^3$, $T^4$ and $T^5$ are each independently hydrogen or $C_1$–$C_{12}$-alkyl, with or without halogen, amino, $C_1$–$C_{12}$-alkoxy, phenyl, substituted phenyl, carboxyl, $C_1$–$C_{12}$-alkoxycarbonyl or cyano substitution,
with the proviso that the ring positions of the substituents J—$T^1$ and $T^4$ within an azulene ring may also be interchanged in either or both of the azulene rings when $T^5$ is hydrogen.

Suitable squaric acid dyes further include for example those compounds which conform to the following formula VIa:

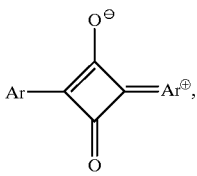

(VIa)

where each Ar is independently an unsubstituted or $C_1$–$C_{20}$-alkoxy-, $C_1$–$C_{20}$-alkylamino-, $C_1$–$C_{20}$-dialkylamino- or $C_1$–$C_{20}$-alkylthio-substituted, aromatic or heteroaromatic five- or six-membered ring, e.g., phenyl, naphthyl, thiophene, pyridine or thiazole. The alkyl groups may each be interrupted by from 1 to 4 oxygen atoms in ether function and may be substituted by phenyl.

Ar is preferably phenyl, which is monosubstituted, disubstituted or trisubstituted by the radicals mentioned in the 2-, 2,4- or 2,4,6-position. Preferably, when the phenyl is polysubstituted, these radicals are identical. Of particular interest are those compounds in which the two Ar's are identical.

Suitable croconic acid dyes are for example those compounds which U.S. Pat. No. 5,526,516 shows under the general formula IV and recites exemplarily in Table 5.

Any alkyl, alkylene or alkenyl appearing in the above-mentioned formulae may be straight-chain or branched.

In the formula Ia, II, III, IV or VIa, suitable $C_1$–$C_{20}$-alkyl radicals, which may be interrupted by from 1 to 4 oxygen atoms in ether function, are for example methyl, ethyl, propyl, isopropyl, butyl, isobutyl, sec-butyl, tert-butyl, pentyl, isopentyl, neopentyl, tert-pentyl, hexyl, 2-methylpentyl, heptyl, octyl, 2-ethylhexyl, isooctyl, nonyl, isononyl, decyl, isodecyl, undecyl, dodecyl, tridecyl, 3,5,5,7-tetramethylnonyl, isotridecyl (the above designations isooctyl, isononyl, isodecyl and isotridecyl are trivial names and are derived from the alcohols obtained by the oxo process—cf. Ullmanns Encyklopädie der technischen Chemie, 4th edition, volume 7, pages 215 to 217, and also volume 11, pages 435 and 436), tetradecyl, pentadecyl, hexadecyl, heptadecyl, octadecyl, nonadecyl, eicosyl, 2-methoxyethyl, 2-ethoxyethyl, 2-propoxyethyl, 2-isopropoxyethyl, 2-butoxyethyl, 2- or 3-methoxypropyl, 2- or 3-ethoxypropyl, 2- or 3-propoxypropyl, 2- or 3-butoxypropyl, 2- or 4-methoxybutyl, 2- or 4-ethoxybutyl, 2- or 4-propoxybutyl, 2- or 4-butoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 4,8-dioxadecyl, 3,6,8-trioxadecyl, 3,6,9-trioxaundecyl, 3,6,9,12-tetraoxatridecyl or 3,6,9,12-tetraoxatetradecyl.

In the formula Ia or II, suitable $C_3$–$C_{10}$-cycloalkyl radicals are branched or unbranched cycloalkyl radicals, which may be interrupted by from 1 to 4 oxygen atoms in ether function, e.g., cyclopropyl, cyclobutyl, cyclopentyl, tetrahydrofuranyl, cyclohexyl, tetrahydropyranyl, cycloheptyl, oxepanyl, 1-methyl-cyclopropyl, 1-ethylcyclopropyl, 1-propylcyclopropyl, 1-butyl-cyclopropyl, 1-pentylcyclopropyl, 1-methyl-1-butylcyclopropyl, 1,2-dimethylcyclopropyl, 1-methyl-2-ethylcyclopropyl, cyclooctyl, cyclooctyl or cyclodecyl.

In the formula Ia, Ib or II, suitable $C_6$–$C_{20}$-aryl radicals in AlO—$C_6$–$C_{20}$-aryl-, Al—NH—$C_6$–$C_{20}$-aryl- or AlN(—$C_6$–$C_{20}$-aryl)$_2$- groups of $Me^1$ and $Me^2$ are for example phenyl optionally substituted by up to two $C_1$–$C_7$-alkyl, by up to three $C_1$–$C_4$-alkyl, by up to four $C_1$–$C_3$-alkyl or by up to five methyl or ethyl radicals, or naphthyl optionally substituted by up to two $C_1$–$C_5$-alkyl, by up to three $C_1$–$C_3$-alkyl or by up to four methyl or ethyl radicals, these optionally present alkyl substituents already being mentioned among the above-recited $C_1$–$C_{20}$-alkyl radicals.

In the formula Ia, Ib or II, suitable N—Het in the AlN—Het groups of $Me^1$ and $Me^2$ is derived for example, from pyrrole, pyrrolidine, pyrazole, pyrazolidine, imidazole, imidazoline, 1H-1,2,3-triazole, 1,2,3-triazolidine, 1H-1,2,4-triazole, 1,2,4-triazolidine, pyridine, piperidine, pyrazine, piperazine, pyridazine, morpholine, 1H-azepine, 2H-azepine, azepan, oxazole, oxazolidine, thiazole, thiazolidine, 1,2,3-, 1,2,4- or 1,3,4-oxadiazole, 1,2,3-, 1,2,4- or 1,3,4-oxadiazolidine, 1,2,3-, 1,2,4- or 1,3,4-thiadiazole or 1,2,3-, 1,2,4- or 1,2,4-thiadiazolidine, the heterocyclic rings being unsubstituted or monosubstituted, disubstituted or trisubstituted by $C_1$–$C_4$-alkyl, phenyl, benzyl or phenylethyl. Corresponding, optional $C_1$–$C_4$-alkyl radicals were mentioned above in connection with the $C_1$–$C_{20}$-alkyl radicals.

In the formula Ia or II, suitable heterocyclic, ring-shaped radicals for $R^1$ to $R^{16}$ or for $Y^1$ to $Y^8$ are derived from heterocyclic, saturated five-, six- or seven-membered rings which may additionally contain one or two further nitrogen atoms and/or a further oxygen or sulfur atom in the ring, e.g., pyrrolidine, pyrazolidine, imidazoline, 1,2,3-triazolidine, 1,2,4-triazolidine, piperidine, piperazine, morpholine, azepan, oxazolidine, thiazolidine, 1,2,3-, 1,2,4- or 1,3,4-oxadiazolidine, or 1,2,3-, 1,2,4- or 1,3,4-thiadiazolidine, the heterocyclic rings being unsubstituted or monosubstituted, disubstituted or trisubstituted by $C_1$–$C_4$-alkyl, phenyl, benzyl or phenylethyl. Corresponding, $C_1$–$C_4$-alkyl radicals were mentioned above in connection with the $C_1$–$C_{20}$-alkyl radicals.

In the formula I, II or VIa, suitable phenyl-substituted $C_1$–$C_{20}$-alkyl is for example benzyl or 1- or 2-phenylethyl.

In the formula II, III, IV or VIa, suitable $C_1$–$C_{20}$-alkoxy radicals, which may be interrupted by from 1 to 4 oxygen atoms in ether function, are for example methoxy, ethoxy, propoxy, isopropoxy, butoxy, isobutoxy, pentyloxy, hexyloxy, heptyloxy, octyloxy, 2-ethylhexyloxy, isooctyloxy, nonyloxy, isononyloxy, decyloxy, isodecyloxy, undecyloxy, dodecyloxy, tridecyloxy, isotridecyloxy, tetradecyloxy, pentadecyloxy, hexadecyloxy, heptadecyloxy, octadecyloxy, nonadecyloxy, eicosyloxy, 2-methoxyethoxy, 2-ethoxyethoxy, 2-propoxyethoxy, 2-isopropoxyethoxy, 2-butoxyethoxy, 2- or 3-methoxypropoxy, 2- or 3-ethoxypropoxy, 2- or 3-propoxypropoxy, 2- or 3-butoxypropoxy, 2- or 4-methoxybutoxy, 2- or 4-ethoxybutoxy, 2- or 4-propoxybutoxy, 2- or 4-butoxybutoxy, 3,6-dioxaheptyloxy, 3,6-dioxaoctyloxy, 4,8-dioxanonyloxy, 3,7-dioxaoctyloxy, 3,7-dioxanonyloxy, 4,7-dioxaoctyloxy, 4,7-dioxanonyloxy, 4,8-dioxadecyloxy, 3,6,8-trioxadecyloxy, 3,6,9-trioxaundecyloxy, 3,6,9,12-tetraoxatridecyloxy or 3,6,9,12-tetraoxatetradecyloxy.

In the formula II or VIa, suitable phenyl-substituted $C_1$–$C_{20}$-alkoxy is for example benzyloxy or 1- or 2-phenylethoxy.

In the formula Ia, III or VI, suitable substituted phenyl is for example $C_1$–$C_6$-alkyl-, $C_1$–$C_6$-alkoxy-, hydroxyl- or halogen-substituted phenyl. The number of substituents can generally be from 1 to 3. In particular, the phenyl is substituted by 1 or 2 $C_1$–$C_6$-alkyl or $C_1$–$C_6$-alkoxy substituents. In the case of monosubstitution, the substituent is preferably in the para-position. In the case of disubstitution, the substituents are preferably in the 2,3-, 2,4-, 3,4- and 3,5-position.

Halogen in the formula Ib, II, IV or VI is for example fluorine, chlorine or bromine.

W in the formula Ia and $X^2$ or $X^3$ in the formula Ib are for example methylimino, ethylimino, propylimino, isopropylimino or butylimino.

$R^1$ to $R^{16}$ in the formula Ia and also $Y^9$ to $Y^{12}$ in the formula II are for example dimethylsulfamoyl, diethylaulfamoyl, diprgpylsulfamoyl, dibutylsulfamoyl or N-methyl-N-ethylsulfamoyl.

$C_2$–$C_{20}$-Alkenyl and also $C_4$–$C_{20}$-alkanedienyl in the formula II are each for example vinyl, allyl, prop-1-en-1-yl, methallyl, ethallyl, but-3-en-1-yl, pentenyl, pentadienyl, hexadienyl, 3,7-dimethylocta-1,6-dien-1-yl, undec-10-en-1-yl, 6,10-dimethylundeca-5,9-dien-2-yl, octadec-9-en-1-yl, octadeca-9,12-dien-1-yl, 3,7,11,15-tetramethylhexadec-1-en-3-yl or eicos-9-en-1-yl.

$C_3$–$C_{20}$-Alkenyloxy in the formula II is for example allyloxy, methallyloxy, but-3-en-1-yloxy, undec-10-en-1-yloxy, octadec-9-en-1-yloxy or eicos-9-en-1-yloxy.

$Z^6$ in the formula IV is for example formyl, acetyl, propionyl, butyryl, isobutyryl, pentanoyl, hexanoyl, heptanoyl, octanoyl or 2-ethylhexanoyl.

If the rings A and/or B in the formula V are substituted, suitable substituents are for example $C_1$–$C_6$-alkyl, phenyl-$C_1$–$C_6$-alkoxy, phenoxy, halogen, hydroxyl, amino, $C_1$–$C_6$-mono- or -dialkylamino or cyano. The number of substituents on the rings is generally from 1 to 3.

$E^3$, $E^4$, $Q^1$ and $Q^2$ in the formula V are each for example methyl, ethyl, propyl, isopropyl, butyl, isobutyl, sec-butyl, pentyl, isopentyl, neopentyl, tert-pentyl or hexyl.

$Q^1$ and $Q^2$ may also be for example hexyl, 2-methylpentyl, heptyl, octyl, 2-ethylhexyl, isooctyl, nonyl, isononyl, decyl, isodecyl, undecyl, dodecyl, cyclopentyl, cyclohexyl, 2-methoxyethyl, 2-ethoxyethyl, 2- or 3-methoxypropyl, 2- or 3-ethoxypropyl, 2-hydroxyethyl, 2- or 3-hydroxypropyl, 2-chloroethyl, 2-bromoethyl, 2- or 3-chloropropyl, 2- or 3-bromopropyl, 2-carboxyethyl, 2- or 3-carboxypropyl, 2-methoxycarbonylethyl, 2-ethoxycarbonylethyl, 2- or 3-methoxycarbonylpropyl, 2- or 3-ethoxycarbonylpropyl, 2-acryloyloxyethyl, 2- or 3-acryloyloxypropyl, 2-methacryloyloxyethyl, 2- or 3-methacryloyloxypropyl, 2-hydroxy-sulfonylethyl, 2- or 3-hydroxysulfonylpropyl, 2-acetylaminoethyl, 2- or 3-acetylaminopropyl, 2-methylcarbamoylethyl, 2-ethylcarbamoylethyl, 2- or 3-methylcarbamoylpropyl, 2- or 3-ethylcarbamoylpropyl, 2-methylcarbamoyloxyethyl, 2-ethylcarbamoyloxyethyl, 2- or 3-methylcarbamoyloxypropyl, 2- or 3-ethylcarbamoyloxypropyl, 2-(trimethylammonium)ethyl, 2-(triethylammonium)ethyl, 2- or 3-(trimethylammonium)propyl, 2- or 3-(triethylammonium)propyl, 2-(triphenylphosphonium)ethyl or 2- or 3-(triphenylphosphonium)propyl.

$A^{n\ominus}$ in the formula IV or V is derived for example from anions of organic or inorganic acids. Particular preference in this connection is given for example to methanesulfonate, 4-methylbenzenesulfonate, acetate, trifluoroacetate, heptafluorobutyrate, chloride, bromide, iodide, perchlorate, tetrafluoroborate, nitrate, hexafluorophosphate or tetraphenylborate.

J in the formula VI is for example methylene, ethylene, 1,2- or 1,3-propylene, 1,2-, 1,3-, 2,3- or 1,4-butylene, pentamethylene, hexamethylene, heptamethylene, octamethylene, nonamethylene, decamethylene, undecamethylene or dodecamethylene.

$T^2$, $T^3$, $T^4$ and $T^5$ in the formula VI are each for example methyl, ethyl, propyl, isopropyl, butyl, isobutyl, sec-butyl, tert-butyl, pentyl, isopentyl, neopentyl, tert-pentyl, 2-methylbutyl, hexyl, 2-methylpentyl, heptyl, octyl, 2-ethylhexyl, isooctyl, nonyl, isononyl, decyl, undecyl, dodecyl, fluoromethyl, chloromethyl, difluoromethyl, trifluoromethyl, trichloromethyl, 2-fluoroethyl, 2-chloroethyl, 2-bromoethyl, 1,1,1-trifluoroethyl, heptafluoropropyl, 4-chlorobutyl, 5-fluoropentyl, 6-chlorohexyl, cyanomethyl, 2-cyanoethyl, 3-cyanopropyl, 2-cyanobutyl, 4-cyanobutyl, 5-cyanopentyl, 6-cyanohexyl, 2-aminoethyl, 2-aminopropyl, 3-aminopropyl, 2-aminobutyl, 4-aminobutyl, 5-aminopentyl, 6-aminohexyl, 2-hydroxyethyl, 2-hydroxypropyl, 3-hydroxypropyl, 2-hydroxybutyl, 4-hydroxybutyl, 5-hydroxypentyl, 6-hydroxyhexyl, 2-methoxyethyl, 2-ethoxyethyl, 2-propoxyethyl, 2-isopropoxyethyl, 2-butoxyethyl, 2-methoxypropyl, 2-ethoxypropyl, 3-ethoxypropyl, 4-ethoxybutyl, 4-isopropoxybutyl, 5-ethoxypentyl, 6-methoxyhexyl, benzyl, 1-phenylethyl, 2-phenylethyl, 4-chlorobenzyl, 4-methoxybenzyl, 2-(4-methylphenyl)ethyl, carboxymethyl, 2-carboxyethyl, 3-carboxypropyl, 4-carboxybutyl 5-carboxypentyl, 6-carboxyhexyl, methoxycarbonylmethyl, ethoxycarbonylmethyl, 2-methoxycarbonylethyl, 2-ethoxycarbonylethyl, 3-methoxycarbonylpropyl, 3-ethoxycarbonylpropyl, 4-methoxycarbonylbutyl, 4-ethoxycarbonylbutyl, 5-methoxycarbonylpentyl, 5-ethoxycarbonylpentyl, 6-methoxycarbonylhexyl or 6-ethoxycarbonylhexyl.

$T^1$ in the formula VI is for example methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, tert-pentyloxycarbonyl, hexyloxycarbonyl, heptyloxycarbonyl, octyloxycarbonyl, isooctyloxycarbonyl, nonyloxycarbonyl, isononyloxycarbonyl, decyloxycarbonyl, isodecyloxycarbonyl, undecyloxycarbonyl, dodecyloxycarbonyl, methoxy, ethoxy, propoxy, isopropoxy, butoxy, isobutoxy, pentyloxy, hexyloxy, acetylamino, carbamoyl, mono- or dimethylcarbamoyl, mono- or diethylcarbamoyl, monocyclohexylcarbamoyl, phenylcarbamoyl, dimethylcarbamoyloxy or diethylcarbamoyloxy.

Particularly noteworthy markers further include the naphthalocyanines of the formula IIa

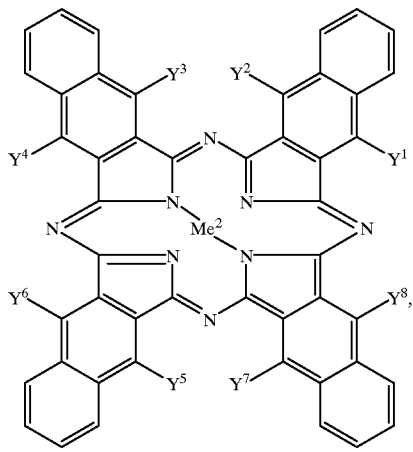

(IIa)

where
$Y^1, Y^2, Y^3, Y^4, Y^5, Y^6, Y^7$ and $Y^8$ are each independently hydrogen, hydroxyl, $C_1$–$C_4$-alkyl or $C_1$–$C_{20}$-alkoxy and
$Me^2$ is $Me^1$ or the radical

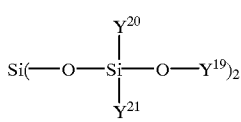

where $R^{19}$ is $C_1$–$C_{13}$-alkyl or $C_{10}$–$C_{20}$-alkadienyl and $Y^{20}$ and $Y^{21}$ are each independently $C_1$–$C_{13}$-alkyl or $C_2$–$C_4$-alkenyl.

Of particular note in this connection are naphthalocyanines of the formula IIa, where $Y^1, Y^2, Y^3, Y^4, Y^5, Y^6, Y^7$ and $Y^8$ are each independently hydroxyl, $C_1$–$C_{20}$-alkoxy, especially $C_1$–$C_{10}$-alkoxy. The alkoxy radicals can be identical or different. Of particular note are further naphthalocyanines of the formula IIa where $Me^2$ is two hydrogens.

Particularly noteworthy markers further include nickel-dithiolene complexes of the formula III where $L^1, L^2, L^3$ and $L^4$ are each independently phenyl, $C_1$–$C_{20}$-alkylphenyl, $C_1$–$C_{20}$-alkoxyphenyl or hydroxyl- or $C_1$–$C_{20}$-alkyl-substituted phenyl, or $L^1$ and $L^2$ and also $L^3$ and $L^4$ are each together the radical of the formula

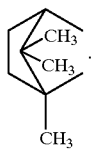

Of particular note in this connection are nickel-dithiolene complexes of the formula III where $L^1$ and $L^4$ are each phenyl and $L^2$ and $L^4$ are each a radical of the formula 4-$[C_2H_5$–$C(CH_3)_2]$—$C_6H_4$.

The markers used in the process of the invention and in the preferred embodiments are preferably the above-shown phthalocyanines of the formula Ia and also the phthalocyanines recited in Table 3 of U.S. Pat. No. 5,525,516, the above-shown naphthalocyanines of the formula II, the naphthalocyanines recited in Table 4 of U.S. Pat. No. 5,525,516 and particularly preferably the above-shown naphthalocyanines of the formula IIa. Of particular note in this connection are phthalocyanines and naphthalocyanines where $Me^1$ or $Me^2$ is two hydrogens.

The region of the spectrum which extends from 600 to about 850 nm is customarily covered with phthalocyanines and the region of the spectrum above about 800 nm customarily with naphthalocyanines.

The phthalocyanines of the formula Ia are known per se and described for example in DE-B-1 073 739 or EF-A-155 780 or are obtainable by conventional methods as used for preparing phthalocyanines or naphthalocyanines and as described for example in F. H. Moser, A. L. Thomas "The Phthalocyanines", CRC Press, Boca Rota, Fla., 1983, or J. Am. Chem. Soc. Volume 106, pages 7404 to 7410, 1984. The phthalocyanines of the formula Ib are likewise known per se and described for example in EP-A-155 780 or obtainable by the methods of the above-cited prior art (Moser, J. Am. Chem. Soc.).

The naphthalocyanines of the formula II are likewise known per se and described for example in EP-A-336 213, EP-A-358 080, GB-A-2 168 372 or GB-A-2 200 650 or obtainable by the methods of the above-cited prior art (Moser, J. Am. Chem. Soc.).

The nickel-dithiolene complexes of the formula III are likewise known per se and described for example in EP-A-192 215.

The aminium compounds of the formula IV are likewise known per se and described, for example, in U.S. Pat. No. 3,484,467 or obtainable by the methods mentioned therein.

The methine dyes of the formula V are likewise known per se and described for example in EP-A-464 543 or obtainable by the methods mentioned therein.

The preparation of the squaric acid dyes is described in U.S. Pat. Nos. 5,525,516 and 5,703,229 and the references which each cites.

The preparation of the croconic acid dyes is described in U.S. Pat. No. 5,525,516 and the references cited therein.

The azulenesquaric acid dyes of the formula VI are likewise known per se and described for example in EP-A-310 080 or U.S. Pat. No. 4,990,649 or obtainable by the methods mentioned therein.

Liquids markable by the method of the invention using a combination of at least two of the above-identified compounds as markers are customarily organic liquids, for example
  alcohols, such as methanol, ethanol, propanol, isopropanol, butanol, isobutanol, sec-butanol, pentanol, isopentanol, neopentanol or hexanol,
  glycols, such as 1,2-ethylene glycol, 1,2- or 1,3-propylene glycol, 1,2-, 2,3- or 1,4-butylene glycol, di- or triethylene glycol or di- or tripropylene glycol,
  ethers, such as methyl tert-butyl ether, 1,2-ethylene glycol monomethyl ether, 1,2-ethylene glycol dimethyl ether, 1,2-ethylene glycol monoethyl ether, 1,2-ethylene glycol diethyl ether, 3-methoxypropanol, 3-isopropoxypropanol, tetrahydrofuran or dioxane,
  ketones, such as acetone, methyl ethyl ketone or diacetone alcohol, esters, such as methyl acetate, ethyl acetate, propyl acetate or butyl acetate, aliphatic or aromatic hydrocarbons such as pentane, hexane, heptane, octane, isooctane, petroleum ether, toluene, xylene, ethyl benzene, tetralin, decalin, dimethylnaphthalene, white spirit, natural oils, such as olive oil, soybean oil or sunflower oil, or natural or synthetic engine, hydraulic or gear oils, for example automotive vehicle engine oil or sewing machine oil, or brake fluids and mineral oils, such as gasoline, kerosine, diesel oil or heating oil.

The abovementioned compounds are particularly useful for marking mineral oils where some form of identification is mandatory, for example for tax reasons. To keep the costs for this to a minimum, but also to minimize possible interactions of the marked mineral oils with any other ingredients present, it is desirable to keep the amount of markers as small as possible. A further reason for keeping the amount of markers as small as possible can be to suppress their possible damaging effects, for example on the fuel intake and exhaust gas outlet region of internal combustion engines.

As already mentioned above, it is generally desirable to mark liquids using marker compounds which produce a high fluorescence quantum yield, i.e., which reemit a large proportion of the absorbed quanta of radiation as fluorescence light quanta.

These compounds to be used as markers are added to the liquids in such amounts that reliable detection is ensured. The (weight-based) total amount of markers in the marked liquid is usually within the range from about 0.1 to 5000 ppb, preferably within the range from 1 to 2000 ppb, particularly preferably within the range from 1 to 1000 ppb.

To mark the liquids, the compounds identified above as markers, or, to be more precise, the combination of at least two markers, are generally added in the form of a (stock) solution. In the case of mineral oils especially, the solvents for preparing these stock solutions are preferably aromatic hydrocarbons, such as toluene, xylene or higher boiling aromatic mixtures.

To avoid such stock solutions having too high a viscosity (and hence poor meterability and handleability), the total concentration of markers is generally set within the range from 0.5 to 50% by weight, based on the total weight of these stock solutions.

The present invention further provides a method for detecting markers in liquids marked by the method of the invention or its preferred embodiments, which comprises using light sources which emit radiation in the absorption ranges of said markers and detecting the fluorescent light reemitted by said markers, at least one of said light sources emitting radiation in the overlapping absorption range of at least one marker with that of at least one other marker and the number of light sources being less than or equal to the number of markers.

The following definitions shall apply: the marker $M\mu$'s wavelength range(s) wherein the extinction coefficient amounts to x% or more of the value at the absorption maximum of the marker $M\mu$ shall be designated "x% wavelength interval" $L\mu(x)$. Since, for example, the number n of markers is in the preferred embodiments from 2 to 10 or from 2 to 6 or from 2 to 4, $\mu$ can accordingly assume integral numerical valves from 1 to 10 or from 1 to 6 or from 1 to 4, respectively (corresponding respectively to the markers M1, M2, M3, ..., M9, M10 or M1, M2, M3, ..., M5, M6 or M1, M2, M3, M4). The corresponding intervals are then respectively L1(x), L2(x), ..., L9(x), L10(x) or L1(x), L2(x), ..., L5(x), L6(x) or L1(x), L2(x), L3(x), L4(x). These intervals are generally connected, but can also be unconnected. For instance, a specific interval $L\mu(x)$ can also consist of two or more subintervals, in which case their totality (union set) is then designated $L\mu(x)$.

Depending on the markers and/or liquid to be marked, the value oil x can be chosen individually or be used to "define" the absorption range of the marker $M\mu$ as a function of the specific requirements. In the case of high absorption by the liquid to be marked, for instance, values of, for example, 10, 20, 25 or even 50 can be sensible for x. Conversely, x values of, for example, 5 or 3 can be sufficient in the case of markers having high absorption power and/or liquids to be marked which have little if any absorption in the contemplated wavelength range. In accordance with these x values, for example, L3(10), L3(20) and L3(25) signify wavelength intervals in which the extinction coefficient of marker M3 is at least, respectively, 10%, 20% or 25% of the value at the absorption maximum of M3. Similarly, L3(5) and L3(3), for example, are used to define wavelength intervals in which the extinction coefficient of marker M3 is at least, respectively, 5% and 3% of the value at the absorption maximum of M3. It can even be sensible to use different x values within an ensemble of markers. For simplicity, $L\mu(x)$ (representing the x% interval of the marker $M\mu$) is hereinbelow merely written as $L\mu$.

The definition of the intervals $L\mu(x)$ of the various markers $M\mu$ contemplated for marking according to the invention is further founded on their respective absorption spectra, determined under comparable conditions, that have been corrected with regard to the blank value of the solvent used in the determination.

In line with the above observations, the wavelength interval in which the absorption maximum of marker $M\mu$ is positioned can likewise be designated as interval $L\mu(x)$. In this case, x can then assume values of, for example, 80, 90, 95 or even 99, as required.

The illustrative case of six different markers M1, M2, M3, M4, M5 and M6, which corresponds to a preferred embodiment in which the number n of the markers assumes the value six, results in the intervals L1, L2, L3, L4, L5 and L6. The regions of overlap of the intervals are, in mathematical terms, their intersections and are herein accordingly designated as $L\mu v$. They can be systematically listed as:

$L1 \cap L2 = L12$ ($\mu=1$, $v=2$), $L1 \cap L3 = L13$ ($\mu=1$, $v=3$), $L1 \cap L4 = L14$ ($\mu=1$, $v=4$), $L1 \cap L5 = L15$ ($\mu=1$, $v=5$), $L1 \cap L6 = L16$ ($\mu=1$, $v=6$), $L2 \cap L3 = L23$ ($\mu=2$, $v=3$), $L2 \cap L4 = L24$ ($\mu=2$, $v=4$), $L2 \cap L5 = L25$ ($\mu=2$, $v=5$), $L2 \cap L6 = L26$ ($\mu=2$, $v=6$), $L3 \cap L4 = L34$ ($\mu=3$, $v=4$), $L3 \cap L5 = L35$ ($\mu=3$, $v=5$), $L3 \cap L6 = L36$ ($\mu=3$, $v=6$), $L4 \cap L5 = L45$ ($\mu=4$, $v=5$), $$L4 \cap L6 = L46 \ (\mu=4, \nu=6)$$

and $$L5 \cap L6 = L56 \ (\mu=5, \nu=6).$$

The regions of overlap of the intervals $L\mu$ with themselves ($L\mu\nu$ where $\nu=\mu$) can be defined analogously:

$$L1 \cap L1 = L11 = L1 \ (\mu=1, \nu=1),$$

$$L2 \cap L2 = L22 = L2 \ (\mu=2, \nu=2),$$

$$L3 \cap L3 = L33 = L3 \ (\mu=3, \nu=3),$$

$$L4 \cap L4 = L44 = L4 \ (\mu=4, \nu=4),$$

$$L5 \cap L5 = L55 = L5 \ (\mu=5, \nu=5)$$

and $$L6 \cap L6 = L66 = L6 \ (\mu=6, \nu=6).$$

The number N of the possible regions of overlap between any two markers among a total of n markers generally works out as $N=n/2\cdot(n-1)$. In the present case of n equal 6, therefore, the above-recited 15 overlapping intervals are obtained. It will be appreciated that the respective regions of overlap $L\nu\mu$ (e.g., L34) are of course equivalent to the regions of overlap $L\nu\mu$ (e.g., L43) and will therefore not be considered any further.

According to the invention, the absorption range of at least one marker shall overlap with the absorption range of at least one further marker. For the example of the six markers M1 to M6 this means that at least one of the 15 regions of overlap must be a non-empty set.

The possibilities are as follows, for example:

A) All adjacent wavelength intervals $L\mu$ and $L(\mu+1)$ form non-empty overlaps (intersections); all nonadjacent wavelength intervals $L\mu$ and $L\nu$ ($\nu>\mu+1$) have no "higher" overlaps (intersections), i.e., form empty sets in each case, viz:

$$L\mu\nu \neq \{\emptyset\}$$

for $\nu=\mu+1$ or $\nu=\mu-1$ and $$L\mu\nu = \{\emptyset\}$$

for $\nu \neq \mu+1$ and $\nu \neq \mu-1$ ("higher" overlaps).

This means in the above, illustrative case that the only existing overlaps are L12, L23, L34, L45 and L56 (and, of course L11, L22, L33, L44, L55 and L66 equivalently to the intervals L1, L2, L3, L4, L5 and L6). All the other overlaps are empty sets. By using five light sources which emit in these regions of overlap, therefore, all six markers M1 to M6 can be excited to reemit fluorescent light, in which case each light source excites two markers at one and the same time. In general, n-1 light sources which emit in the regions L12, L23, . . . , L(n-2)(n-1) and L(n-1)n will excite n markers $M\mu$. Furthermore, the markers M1 and Mn (e.g., M6) will each have only a single region of overlap (L12 or L(n-1)n, e.g., L56), while the other markers (e.g. M2 to M5) will each have two regions of overlap (e.g., $M\mu$ has the regions $L(\mu-1)\mu$ and $L\mu(\mu+1)$.

At least one marker $M\mu$ will have a wavelength interval $L\mu$ which intersects with the wavelength interval $L(\mu+2)$ of the marker $M(\mu+2)$ to form a "higher" overlap $L\mu(\mu+2)$. If this "higher" region of overlap overlaps with the wavelength interval $L(\mu+1)$ of the marker $M(\mu+1)$ which will generally be the case, this will produce a "triple" overlap $L\mu(\mu+1)(\mu+2)$ of the intervals $L\mu$, $L(\mu+1)$ and $L(\mu+2)$. By using a light source which emits in this region it is therefore possible to excite the markers $M\mu$, $M(\mu+1)$ and $M(\mu+2)$ simultaneously to reemit fluorescent light. In mathematical terms, this can be formulated as:

$$L\mu\nu \neq \{\emptyset\}$$

for $\nu=\mu+2$, i.e., $(L\mu(\mu+2)= ) L\mu \cap L(\mu+2) \neq \{\emptyset\}$, and $$L(\mu+1) \cap [L\mu \cap L(\mu+2)] = L(\mu+1) \cap L\mu \cap L(\mu+2) = L\mu \cap L(\mu+1) \cap L(\mu+2) = L\mu(\mu+1)(\mu+2) \neq \{\emptyset\}.$$

In the above, illustrative case of six markers M1 to M6, this means that there is, for example, a region of overlap L13 which overlaps with the interval L2 (the overlap L22), i.e., forms intersection $(L1 \cap L3) \cap L2 = L1 \cap L3 \cap L2 = L1 \cap L2 \cap L3$, which can be abbreviated, analogously to the above-introduced intersections of two intervals, as intersection L123 of three intervals (or generally as $L\mu\nu\omega$). It is further immediately apparent that:

$$L\mu\nu\omega = L\mu\nu\omega = L\nu\omega\mu = L\nu\mu\omega = L\omega\mu\nu = L\omega\nu\mu,$$

i.e., all "permutated" regions are equivalent to one another.

By using, for example, three light sources which emit in the overlaps L123, L45 and L56, all six markers M1 to M6 can be excited to reemit fluorescent light, with the light source a(L123) simultaneously exciting the markers M1, M2 and M3 and thus light source a(L45) and a(L56) simultaneously exciting, respectively the markers M4 and M5 on the one hand and M5 and M6 on the other. Alternatively, it is also possible, in the latter case, to use a light source which emits, not in the region L56, but only, for example, in the region L66–L56, i.e., in he interval L6 minus the overlap (intersection) between L5 and L6. This will excite only marker M6, but not marker M5.

If there is in addition an overlap L456, just two light sources, each emitting in the regions L123 and L456, respectively, will be sufficient to excite the fluorescent emissions of all six markers M1 to M6, with simultaneous excitation of the markers M1, M2 and M3 on the one hand and M4, M5 and M6 on the other.

In what follows, $M\mu'$ shall designate markers which do not overlap with each other, but which each have absorption maximum wavelengths comparable to the markers $M\mu$.

For a mixture corresponding to the above-discussed scenario A), i.e., a mixture of six markers M1 to M6 having the regions L12, L23, L34, L45 and L56 (and of course the regions L11, L22, L33, L44, L55 and L66 equivalently to the intervals L1, L2, L3, L4, L5 and L6), excitation of all the markers can be achieved with just five suitable light sources (designated $a(L\mu\nu)$, i.e., a(L12), a(L23), a(L34), a(L45) and a(L56)). In contrast, a mixture of six markers M1', M2', M3', M4', M5' and M6' cannot be excited by the light sources a(L12) to a(L56) to reemit fluorescent light. Such a mixture corresponds to a mixture as suggested by the prior art, for example in U.S. Pat. No. 5,525,516.

The same is true of the above-discussed scenario B). Here a single light source a(L123) brings about an excitation of the markers M1, M2 and M3. In the case of the markers M1', M2' and M3' only the marker M2' will be excited if its absorption maximum wavelength is in the region L123. The markers M1' and M3', however, would not be excited by such a light source to reemit fluorescent light.

It is further possible, according to the invention, to mark liquids by using, for example, markers M1 to M6 which have overlaps L123, L34, L55 (=L5) and L66 (=L6). The light sources a(L123), a(L34), a(L55) and a(L66) will excite all the markers. In contrast, in the case of the markers M1' to M6' these light sources will only bring about an excitation of the markers M5', M6' and perhaps M2', but not of the markers M1', M3' and M4'.

Furthermore, according to the invention, it is possible, for example, to use a mixture of markers M1 and M2 which (by definition) has an overlap L12. If, for example, the wavelength interval of the absorption maximum of the marker M1 (this "main absorption range" can be defined as required for example as L1(80), L1(90), L1(95), or L1(99) (see above) falls within the region L12, then it is possible to use two light sources a(L1) and a(L2) which emit in the range of the respective absorption maxima (or the respective "main absorption ranges") of the markers M1 and M2 (e.g. L1(80), L1(90), L1(95) or L1(99) on the one hand and L2(80), L2(90), L2(95) or L2(99) on the other). The intensity of the fluorescence reemitted by M1 is determined completely by the intensity of radiation absorbed from the light source a(L1). In contrast, the intensity of the fluorescent light reemitted by M2 results from the intensity of radiation absorbed by M2 from the light source a(L2) and the light source a(L1) in the region of overlap L12. In the case of a mixture of M1' and M2', the respective intensity of the fluorescent light reemitted by M1' or M2' is completely determined by the intensity of radiation absorbed from the light source a(L1) and a(L2), respectively. Such a mixture of M1' and M2' corresponds to a mixture as suggested by the prior art, for example in U.S. Pat. No. 5,525,516.

It is further possible to use a mixture of markers corresponding to the scenarios A) and/or B) with such markers which have no regions of overlap with the other markers. As further protection against fraudulent misrepresentation, it is also possible to perform the detection of the markers by detecting the fluorescent light excited by various, defined combinations of light sources. This is illustratively embodied hereinbelow without, however, implying any restriction of the invention.

Example 1: The markers M1 to M4 have overlaps L12, L23 and L34. The wavelength intervals L1(x), L2(x), L3(x) and L4(x) which accommodate the respective absorption maxima of the markers M1 to M4 (these "main absorption ranges" can be defined, for example, as $L\mu(x)$ where x is, for example, 80, 90, 95 or 99(%), see above) have no overlap (intersection) with the regions L12, L23 and L34.

Combination 1.1: The light sources a(L1(x)), a(L2(x)), a(L3(x)) and a(L4(x)) are used. The markers reemit their respective fluorescent light. There is no combined excitation of fluorescence.

Combination 1.2: The light sources a(L12), a(L23) and a(L34) are used. The markers reemit their respective fluorescent light due to the combined excitation. a(L12) excites the markers M1 and M2, a(L23) the markers M2 and M3 and a(L34) the markers M3 and M4 to reemit fluorescence. If the markers M1 to M4 are excited simultaneously by the light sources, both the excitation due to a(L12) and a(L23) on the one hand and the excitation due to a(L23) and a(L34) on the other contribute to the intensity of fluorescence of marker M2 and M3, respectively. If the markers are excited by the light sources in succession, then the reemitted fluorescent light is obtained in the form of respective subspectra which show a fluorescent light intensity distribution due to the markers M2 and M3 which differs from the former case. These (three) subspectra, however, can be combined (arithmetically, for example, by means of appropriate computer programs) to form the overall spectrum of the former case. In the general case the intensity distribution of the fluorescent emissions of the markers M1 to M4 of the combination 1.2 (combined excitation) will differ from the intensity distributions of combination 1.1. The sequence of detection in accordance with combinations 1.1 and 1.2 therefore creates a "twofold fingerprint" for the marker mixture or the liquid comprising such a marker mixture. Of course, the light sources described in the combinations 1.1 and 1.2 can also be combined with one another.

Example 2: The markers M1 to M4 have overlaps L12, L23 and L34. The wavelength intervals L1(x), L2(x), L3(x) and L4(x) which accommodate the respective absorption maxima of the markers M1 to M4 (these "main absorption ranges" can be defined, for example, as $L\mu(x)$ where x is, for example, 80, 90, 95 or 99(%), see above) have overlaps (intersections) with the regions L12 L23 and L34, e.g., L12∩L1(x)≠{∅}, L23∩L2(x)≠{∅}, L23∩L3(x)≠{∅} and L34∩L4(x)≠{∅}.

Combination 2.1: The light sources a(L1(x)), a(L2(x)), a(L3(x)) and a(L4(x)) are used. The markers reemit their respective fluorescent light due to the combined excitation. a(L1(x)) excites the markers M1 and M2, a(L2(x)) and a(L3(x)) excite the markers M2 and M3 and a(L4(x)) excites the markers M3 and M4 to reemit fluorescent light.

Combination 2.2: The light sources a(L1(x)), a(L3(x)) and a(L4(x)) are used. The markers reemit their respective fluorescent light due to the combined excitation. a(L1(x)) excites the markers M1 and M2, a(L3(x)) excites the markers M2 and M3 and a(L4(x)) excites the markers M3 and M4 to reemit fluorescent light. With regard to the simultaneous or successive excitation by the light sources, the remarks made in connection with combination 1.2 of Example 1 apply here, too. However, the intensity ratios differ from those arising out of combination 2.1.

Combination 2.3: The light sources a(L12), a(L23) and a(L34) are used. The markers reemit their respective fluorescent light due to the combined excitation. a(L12) excites the markers M1 and M2, a(L23) the markers M2 and M3 and a(L34) the markers M3 and M4 to reemit fluorescence. With regard to the simultaneous or successive excitation by the light sources, the remarks made in connection with combination 1.2 of Example 1 apply here, too. In the general case, the intensity distribution of the fluorescent emissions of the markers M1 to M4 of the combination 2.3 will differ from the intensity distributions of combinations 2.1 and 2.2. The sequence of detection in accordance with combinations 2.1, 2.2 and 2.3 therefore creates a "triple fingerprint" for the marker mixture or the liquid comprising such a marker mixture. Of course, the light sources described in the combinations 2.1, 2.2 and 2.3 can also be combined with one another.

To mark liquids according to the present invention, it is also possible, as will be appreciated, to use combinations of markers which differ in the relative amounts of the markers. For instance, a liquid can be marked with a mixture of the markers, M1 to M4 in a molar ratio of M1:M2:M3:M4= 1:1:1:1, while another liquid can be marked with a mixture in a ratio of, for example, 2:1:1:1, 4:1:1:1, 8:1:1:1, 2:2:1:1, 2:4:1:1, 2:8:1:1, 4:4:1:1, 4:8:1:1, 8:8:1:1, 2:2:2:1, 2:2:4:1, 2:2:8:1, 2:2:2:2, 2:2:2:4, 2:2:2:8 or else in the ratio of an appropriate permutation thereof.

If the intention is to mark different liquids only with different concentrations of a fixed mixture of markers (e.g., M1 to M4), the respective concentration will usually be chosen so that it differs from liquid to liquid by at least a factor of two so that the unambiguity of detection may be safeguarded. However, it is preferable to mark different liquids by using marker mixtures of different molar ratios of the markers relative to one another.

The basic construction for exciting and detecting fluorescence in a liquid marked according to the invention comprises:

a sample cuvette which contains the marked liquid, an excitation unit (A) comprising:

$\alpha_1$) a light source, usually equipped with collimator optics, and $\alpha_2$) usually a plane mirror which is positioned opposite to the light source on that side of the sample cuvette which is remote from the light source, and reflects the transmitted radiation to increase the intensity irradiated into the sample, a detection unit (D) comprising:

$\delta_1$) a photodetector (usually provided with collimator optics) in front of which there are usually positioned optical filters (e.g., cutoff or interference filters) and optionally NIR polarizers and which is disposed in such a way that the fluorescent light reemitted in its direction is incident (or imaged) thereon and detected, and $\delta_2$) usually a concave mirror which is positioned opposite the photodetector on that side of the sample cuvette which is remote from the photodetector, and reflects the fluorescent light reemitted in the opposite direction (away from the photodetector) and hence serves to enhance the sensitivity of detection.

Such a construction is illustrated in principle in WO 94/02570 (differing with regard to the irradiating direction of the light source). The fluorescent light need not be detected perpendicularly, but can be detected at virtually any desired angle with regard to the radiating direction. It is sensible, however, not to contemplate the angles of 0° and 180°.

The observations hereinbelow will operate with the following definitions:

Excitation and detection units in the general sense are designated, respectively, as A and D (see above). Markers in the general sense are designated M.

An excitation unit adjusted by means of an appropriate light source to specifically the wavelength interval $L\mu$(synonymously with the "overlap" $L\mu\mu$ or $L\mu\mu\mu$), the overlap $L\mu\nu$ or the overlap $L\mu\nu\omega$ (i.e., the light source emits radiation in wavelength interval $L\mu$ of marker $M\mu$, in the region of overlap between markers $M\mu$ and $M\nu$ or in the region of overlap between markers $M\mu$, $M\nu$ and $M\omega$) is uniformly referred to as $A(L\mu\nu\omega)$ or shorter $A\mu\nu\omega$, or various such units are referred to as $A\mu_1\nu_1\omega_1, \ldots, A\mu_n\nu_n\omega_n$, where, for example, for n equal 2 to 10 or 2 to 6 or 2 to 4 the parameters $\mu$, $\nu$, and $\omega$ (or $\mu_1, \ldots, \mu_n, \nu_1, \ldots, \nu_n$ and $\omega_1, \ldots, \omega_n$) can each assume values of, respectively, 1 to 10, 1 to 6 and 1 to 4.

Of course, a plurality of the units $A\mu\nu\omega$ would be equivalent due to the definition of $L\mu\nu\omega$, as already mentioned above. For example, by virtue of the definition of L123 as L1∩L2∩L3 (=L3∩L1∩L2=L2∩L3∩L1=L2∩L1∩L3=L1∩L3∩L2 =L3∩L2∩L1) the units A123 ($\mu_1$=1, $\nu_2$=2 and $\omega_3$=3), A312 ($\mu_3$=3, $\nu_1$=1 and $\omega_2$=2), A231 ($\mu_2$=2, $\nu_3$=3 and $\omega_1$=1), A213 ($\mu_2$=2, $\nu_1$=1 and $\omega_3$=3), A132 ($\mu_1$=1, $\nu_3$=3 and $\omega_2$=2) and A321 ($\mu_3$=3, $\nu_2$=2 and $\omega_1$=1) are identical. These further units which are identical to a single unit shall not be further contemplated, as in the case of the equivalent overlaps $L\mu\nu$ and $L\nu\mu$ for the definition of the regions of overlap given at the outset.

Of course, higher "overlaps", e.g., $L\mu\nu\omega\chi$ etc. and appropriate light sources $A\mu\nu\omega\chi$ etc., are possible. However, these shall not be considered any further here.

$A\mu$, $A\mu\mu$ and $A\mu\mu\mu$ must be considered synonymous nomenclatures and signify identical excitation units which emit radiation in the wavelength interval $L\mu$ (=$L\mu\mu$=$L\mu\mu\mu$) of the marker $M\mu$.

A specific detection unit which, for example by means of appropriate optical filters (and optionally polarizers) is specifically adjusted to the reemitted fluorescent light from one of the markers $M\mu$ is designated $D\mu$ (or else as detection channel $\mu$).

Thus, for example, the three markers M1, M2 and M3 can be assigned the excitation units A1 (=A11=A111), A2 (=A22=A222), A3 (=A33=A333), A12 (=A112=A122), A13 (=A113=A133), A23 (=A223=A233) and A123 and the adapted detection units D1, D2 and D3.

Furthermore, it is also possible, for example for two markers M1 and M2 (if there is a region of overlap L12), for the fluorescence of said markers M1 and M2 to be excited by means of the identical unit A12. The fluorescent light is then detected by means of the respective units D1 and D2. The combinations of excitation and detection can then be written as A12/D1 and A12/D2.

If, within an excitation unit A, the adaptation to the respective overlap $L\mu\nu\omega$ merely takes place through the use of an appropriate light source $\alpha_1\mu\nu\omega$ (i.e., the latter emitting radiation in the wavelength interval $L\mu$ of the marker $M\mu$, in the region of overlap between markers $M\mu$ and $M\nu$ or in the region of overlap between markers $M\mu$, $M\nu$ and $M\omega$), this is designated $A(\mu_1\nu_1\omega_1, \ldots, \mu_n\nu_n\omega_n)$ in the case of n markers, where, for example for n equal to 2 to 10 or 2 to 6 or 2 to 4, the parameters $\mu_1, \ldots, \mu_n, \nu_1, \ldots, \nu_n$ and $\omega_1, \ldots, \omega_n$ can each assume values from 1 to 10 or from 1 to 6 or from 1 to 4, respectively. For example, A(111,112,223) (=A(1,12,23)) signifies an excitation unit which by the use of the light sources $\alpha_1 111$ (=$\alpha_1 1$), $\alpha_1 112$ (=$\alpha_1 12$) and $\alpha_1 223$ (=$\alpha_1 23$) can be adapted to the wavelength interval L1 (the overlap L111) of the marker M1 and the overlaps L12 and L23 of the markers M1 and M2 on the one hand and M2 and M3 on the other.

For a detection unit $D\mu$ where adaptation to the reemitted fluorescent light from the respective marker $M\mu$ is merely effected by the use of appropriate photodetectors and/or optical filters (and optionally polarizers), the designations are in the case of n markers D(1,2), D(1,2,3), etc. through D(1,2,3, ... , 9,10) or D(1,2), D(1,2,3), etc. through D(1,2, ... ,5,6) or D(1,2), D(1,2,3), D(1,2,3,4), respectively, n being here, for example, in turn from 2 to 10 or from 2 to 6 or from 2 to 4, respectively.

If the overlaps $L\mu\nu\omega$ of the n markers $M\mu$, where n is again for example from 2 to 10 or from 2 to 6 or from 2 to 4, are each successively excited with units $A\mu\nu\omega$ respectively adapted thereto and the fluorescent light reemitted by the respective marker $M\mu$ is detected by $D\mu$, this is expressed by the notation "$A\mu_1\nu_1\omega_1$/D1, $A\mu_2\nu_2\omega_2$/D2, ... " etc. through ". . . $A\mu_9\nu_9\omega_9$/D9, $A\mu_{10}\nu_{10}\omega_{10}$/D10" or "$A\mu_1\nu_1\omega_1$/D1, $A\mu_2\nu_2\omega_2$/D2, ... " etc. through ". . . $A\mu_5\nu_5\omega_5$/D5, $A\mu_6\nu_6\omega_6$/D6" or "$A\mu_1\nu_1\omega_1$/D1, $A\mu_2\nu_2\omega_2$/D2, $A\mu_3\nu_3\omega_3$/D3, $A\mu_4\nu_4\omega_4$/D4", respectively.

If the overlaps $L\mu\nu\omega$ of the n markers $M\mu$ are simultaneously excited using an appropriate number of units $A\mu\nu\omega$ and their reemitted fluorescent light is simultaneously detected using n units $D\mu$, this is written "$A\mu_1\nu_1\omega_1$/$A\mu_2\nu_2\omega_2$/ ... /$A\mu_n\nu_n\omega_n$/D1/D2/ ... /Dn".

Note: in line with the above, n or else fewer units $A\mu\nu\omega$ can be present. For simplicity, however, this is written "$A\mu_1\nu_1\omega_1$/$A\mu_2\nu_2\omega_2$/ ... /$A\mu_n\nu_n\omega_n$/".

If the overlaps $L\mu\nu\omega$ of the n markers are simultaneously excited using an appropriate number of units $A\mu\nu\omega$ and the fluorescent light reemitted by the markers $M\mu$ is detected using a unit D, for example a multiwavelength detector (consisting of an optical, dispersive element, for example a prism or diaphragm, and a line or area detector), this is written "$A\mu_1v_1\omega_1/A\mu_2v_2\omega_2/ \ldots /A\mu_nv_n\omega_n/D$".

In essence, a distinction must be made between the marked sample being excited by the units A I) in the same sample volume or II) in different sample volumes.

In case I), the following methods and illustrative constructions for the detection equipment can be used (here n is for example from 2 to 10 or from 2 to 6 or from 2 to 4):

I.1) $A\mu_1v_1\omega_1/D1, A\mu_2v_2\omega_2/D2, \ldots, A\mu_{n-1}v_{n-1}\omega_{n-1}/Dn-1, A\mu_nv_n\omega_n/Dn$ (the n markers $M\mu$ are each excited in the overlaps $L\mu v\omega$ by their corresponding units $A\mu v\omega$ and the fluorescent emissions of the markers $M\mu$ are each detected by the units $D\mu$).

a) The construction corresponds essentially to the construction mentioned at the beginning and illustrated in WO 94/02570. The difference is that appropriate units $A\mu v\omega$ and $D\mu$ are used for each marker $M\mu$. This can take the form of a spatially offset arrangement of a plurality (equal to the number of markers to be detected) of pairs of units $A\mu v\omega$ and $D\mu$ radially around the sample cuvette. The latter then preferably has a circular cross section. The sample volumes (or sample paths) irradiated by the units $A\mu v\omega$ are strictly not identical, however. But the excitation rays (lying in one plane) intersect in a common piece of the sample volume. A plurality of units $A\mu v\omega$ can (and generally are) identical. For instance, in the case of three markers M1 to M3 (e.g., with the overlaps L12 and L23) the appropriate (three) pairs A12/D1, A12/D2 and A23/D3 or else A12/D1, A23/D2 and A23/D3 can be used for excitation and detection. The combination of excitation and detection of the n markers $M\mu$ can take place not only in succession but also simultaneously.

b) The construction corresponds essentially to the construction mentioned at the beginning and illustrated in WO 94/02570. The difference is that the light sources $\alpha_1\mu v\omega$ and photodetectors $\delta_1\mu$ of the units $A\mu v\omega$ and $D\mu$ are each positioned on appropriate carousels (in place of individual plane mirrors $\alpha_2\mu v\omega$ and concave mirrors $\delta_2\mu$ it is sensible in this case to use in each case only one fixed plane or concave mirror). To detect the marker $M\mu$, the corresponding light source $\alpha_1\mu v\omega$ and the corresponding photodetector $\delta_1\mu$ are moved into the excitation and detection position, respectively, by rotation of the respective carousels. The ray trajectory through the marked sample and the irradiated sample volume are identical for each marker to be determined. The combination of excitation and detection of the n markers $M\mu$ can only take place in succession.

c) By using, for example, a cylindrical sample cuvette which can be sealed at either or both ends with windows made of the same material as the cuvette or which is sealed at both ends and preferably has lateral sample inlets and outlets, it is possible to arrive at a modified construction. Similarly to the description under a), the light sources $\alpha_1\mu v\omega$ of the units $A\mu v\omega$ can be positioned on a carousel (in which case it is sensible to use only one fixed plane mirror instead of individual plane mirrors $\alpha_2\mu v\omega$). The respective unit $A\mu v\omega$ then irradiates the sample parallel to the longitudinal axis of the cuvette. The respective units $D\mu$ (this time of course with their respective subunits $\delta_2\mu v\omega$) can be placed radially thereto (and hence always perpendicularly to the radiation direction of the excitation light) around the sample cuvette to detect the fluorescent light reemitted in each case. The combination of excitation and detection of the n markers $M\mu$ can only take place in succession (potentially, of course, the fluorescent light reemitted simultaneously by a plurality of markers can be detected simultaneously by the units $D\mu$).

I.2) A/D1, A/D2, ..., A/Dn−1, A/Dn (all n markers $M\mu$ are simultaneously excited by a "polychromatic" light source and detected by means of their respective detection channel $D\mu$).

a) The construction can be similar to that described in b) under I.1). However, instead of an appropriate carousel for the subunits $\alpha_1\mu v\omega$ only one polychromatic excitation unit A is used. Detection is effected in accordance with the construction described under b) of I.1). The combination of excitation and detection of the n markers $M\mu$ can only take place in succession.

b) If, in line with the construction described in c) under I.1), a cylindrical sample cuvette is used, for example, then the unit A will irradiate the sample parallel to the longitudinal axis of the cuvette. The respective units $D\mu$ can again be placed radially thereto (hence perpendicular to the radiating direction of the excitation light) around the sample cuvette. The combination of excitation and detection of the n markers $M\mu$ can take place both in succession and simultaneously.

I.3) $A\mu_1v_1\omega_1/D, A\mu_2v_2\omega_2/D, \ldots, A\mu_{n-1}v_{n-1}\omega_{n-1}/D, A\mu_nv_n\omega_n/D$ (the n markers $M\mu$ are each excited in the overlaps $L\mu v\omega$ by the corresponding units $A\mu v\omega$ and the fluorescent emissions of the markers $M\mu$ are each detected by the units $D\mu$).

a) The construction can be similar to that described in b) under 1.1). However, instead of an appropriate carousel for the photodetectors $\delta_1\mu$ only one detection unit D, for example a multiwavelength detector is used. Excitation is effected in accordance with the construction described under b) of I.1). The combination of excitation and detection of the n markers $M\mu$ can only take place in succession.

b) If, in line with the construction described in c) under I.1), a cylindrical sample cuvette is used, for example, then the unit D detects the reemitted fluorescent light parallel to the longitudinal axis of the cuvette. The respective units $A\mu v\omega$ (together with their corresponding plane mirrors $\alpha_2\mu v\omega$) can be placed radially thereto (hence perpendicular to the longitudinal axis of the cuvette) around the sample cuvette. The combination of excitation and detection of the n markers $M\mu$ can take place both in succession and simultaneously.

The constructional possibilities mentioned here are consequently comparable to those mentioned in a) and b) of point I.2) and differ only in the spatial interchange of the excitation and detection unit(s).

I.4) $A(\mu_1v_1\omega_1, \mu_2v_2\omega_2, \ldots, \mu_{n-1}v_{n-1}\omega_{n-1}, \mu_nv_n\omega_n)/D1$, $A(\mu_1v_1\omega_1, \mu_2v_2\omega_2, \ldots, \mu_{n-1}v_{n-1}\omega_{n-1}, \mu_nv_n\omega_n)/D2, \ldots$, $A(\mu_1v_1\omega_1, \mu_2v_2\omega_2, \ldots, \mu_{n-1}v_{n-1}\omega_{n-1}, \mu_nv_n\omega_n)/Dn-1$, $A(\mu_1v_1\omega_1, \mu_2v_2\omega_2, \ldots, \mu_{n-1}v_{n-1}\omega_{n-1}, \mu_nv_n\omega_n)/Dn$ (the n markers $M\mu$ are each excited in the overlaps $L\mu v\omega$ and detected by means of their respective detection channel $D\mu$).

a) The construction can be similar to that described in a) under I.2). However, the carousel for the light sources α₁μ is replaced with an excitation unit A which, for example (case a₁), contains interchangeable light sources $a_1\mu\nu\omega$. Furthermore, however, A can also contain a plurality of light sources $\alpha_1\mu\nu\omega$ whose respective irradiation, for example (case a₂), is directed by means of optical fibers or optical fiber bundles or collinear superposition of the individual rays of the light sources by means of optical elements, for example beam splitters, dichroic beam splitters, diaphragms, etc. in such a way that it will respectively enter the sample cuvette at the same location thereof. The respective fluorescent light is detected in accordance with the construction described under a) of I.2). The combination of excitation and detection of the n markers Mμ can only take place in succession.

b) If, in line with the construction described in c) under 1.1), a cylindrical sample cuvette is used, for example, a unit A described under a) (case a₁ or case a₂) will irradiate the sample parallel to the longitudinal axis of the cuvette. The respective units Dμ can again be placed radially thereto (and hence in each case perpendicularly to the radiating direction of the excitation light) around the sample cuvette.

Using the unit A corresponding to case a₁, a combination of excitation and detection of the n markers Mμ can only take place in succession. Using a unit A corresponding to a₂, the combination of excitation and detection of the n markers Mμ can take place in succession and potentially also simultaneously.

I.5) $A\mu_1v_1\omega_1/D(1,2,\ldots,n-1,n)$, $A\mu_2v_2\omega_2/D(1,2,\ldots,n-1,n)$, ..., $A\mu_{n-1}v_{n-1}\omega_{n-1}/D(1,2,\ldots,n-1,n)$, $A\mu_nv_n\omega_n/D(1,2,\ldots,n-1,n)$ (the n markers Mμ are each excited in the overlaps L$\mu\nu\omega$ by their corresponding unit A$\mu\nu\omega$ and detected).

a) The construction can be similar to that described in b) under I.1). Instead of an appropriate carousel for the photodetectors δ₁μ, there is used a detection unit D which for example (case a₁) contains interchangeable photodetectors and/or interchangeable optical filters (and optionally polarizers) δ₁μ. Furthermore, however, D can also contain a plurality of photodetectors δ₁μ to which the respective reemitted fluorescent light is passed for example (case a₂) by means of optical fibers or optical fiber bundles. Excitation takes place in accordance with the construction described under b) of I.1). The combination of excitation and detection of the n markers Mμ can only take place in succession.

b) If, in line with the construction described in c) under 1.1), a cylindrical sample cuvette is used, for example, a unit D described under a) (case a₁ or case a₂) will detect the fluorescent light reemitted in each case parallel to the longitudinal axis of the cuvette. The respective units A$\mu\nu\omega$ can again be placed radially thereto (and hence in each case perpendicularly to the longitudinal axis of the cuvette) around the sample cuvette. Using the unit D corresponding to case a₁, a combination of excitation and detection of the n markers Mμ can only take place in succession. Using a unit D corresponding to a₂, the combination of excitation and detection of the n markers Mμ can take place in succession and potentially also simultaneously.

I.6) $A(\mu_1v_1\omega_1, \mu_2v_2\omega_2, \ldots, \mu_{n-1}v_{n-1}\omega_{n-1}, \mu_nv_n\omega_n)/D(1,2,\ldots,n-1,n)$ (the n markers Mμ are each excited in the overlaps L$\mu\nu\omega$ and detected).

The construction can be effected using an excitation unit A which for example (case a₁) contains interchangeable light sources $\alpha_1\mu\nu\omega$ or light sources $\alpha_1\mu\nu\omega$ whose respective radiation is for example (case a₂) directed by means of optical fibers or optical fiber bundles or collinear superposition of the individual rays of the light sources by means of optical elements for example beam splitters, dichroic beam splitters, diaphragms, etc., in such a way that the radiation enters the sample cuvette in each case at the same location thereof. It is accordingly possible to use a detection unit D which contains for example (case a₁) interchangeable photodetectors and/or interchangeable optical filters (and optionally polarizers) δ₁μ or else a plurality of photodetectors δ₁μ to which the respective reemitted fluorescent light is for example passed (case a₂) by means of optical fibers or optical fiber bundles. For the cases A(case a₁)/D(case a₁), A(case a₁)/D(case a₂) and A(case a₂)/D(case a₁) the combination of excitation and detection of the n markers Mμ can only take place in succession. For case A(case a₂)/D(case a₂) the combination of excitation and detection of the n markers Mμ can take place in succession and potentially also simultaneously.

The geometric relationship between the excitation and detection units here corresponds essentially to the situation described at the beginning and in WO 94/02570.

I.7) $A\mu_1v_1\omega_1/A\mu_2v_2\omega_2/\ldots/A\mu_{n-1}v_{n-1}\omega_{n-1}/A\mu_nv_n\omega_n$/D1/D2/.../Dn-1/Dn (the n markers Mμ are simultaneously excited in the regions of overlap by the corresponding units Aμ and simultaneously detected by the units Dμ).

The simultaneous excitation and detection of the n markers can in principle be carried out using the geometries described under point I.1) in a), point I.2) in b), point I.3) in b), point I.4) in case a₂ of b), point I.5) in case a₂ of b) and point I.6) in case A(case a₂)/D(case a₂).

In case II), i.e., excitation taking place in different sample volumes, the following methods and illustrative ways of constructing the detection equipment can find application (n here assumes for example values from 2 to 10 or from 2 to 6 or from 2 to 4):

II.1) A1/D1, A2/D2, ..., An-1/Dn-1, An/Dn (the n markers Mμ are each excited in the regions of overlap L$\mu\nu\omega$ by the corresponding units A$\mu\nu\omega$ and detected by the respective units Dμ).

The arrangement of the respective pairs A$\mu\nu\omega$/Dμ corresponds essentially to the geometry explained at the beginning and in point I.1) in a) and also illustrated in WO 94/02570. That is, the optical axis of the unit A$\mu\nu\omega$ (corresponding to the direction of the exciting beam) and the optical axis of the corresponding unit Dμ are positioned in a plane to which the longitudinal axis of the sample cuvette is normal. These two optical axes form an angle χ, which is within the range from 0° to 180°, subject to the following definition: on projection in the radiating direction of the unit A$\mu\nu\omega$ this angle shall be +χ or −χ depending on whether the corresponding unit Dμ is positioned respectively to the right or left of this direction of projection. This is symbolized by the notation A$\mu\nu\omega$(+)Dμ and A$\mu\nu\omega$(−)Dμ, respectively; that is, $A\mu_1v_1\omega_1(+)D1$, $A\mu_2v_2\omega_2(+)D2$, $A\mu_3v_3\omega_3(+)D3$, etc. on the one hand and $A\mu_1v_1\omega_1(-)D1$, $A\mu_2v_2\omega_2(-)D2, A\mu_3v_3\omega_3(-)D3$ etc. on the other. The excitation (and detection) of spatially different sample volumes is effected by arranging the respective pairs $A\mu v\omega/D\mu$ in parallel planes. The sequence of the planes can be in the form $A\mu_1v_1\omega_1(+)D1, A\mu_2v_2\omega_2(+)D2, A\mu_3v_3\omega_3(+)D3, \ldots, A\mu_nv_n\omega_n(+)Dn$ (equivalently thereto in the form $A\mu_1v_1\omega_1(-)D1, A\mu_2v_2\omega_2(-)D2, A\mu_3v_3\omega_3(-)D3, \ldots, A\mu_nv_n\omega_n(-)Dn$) or else for example in the form $A\mu_1v_1\omega_1(+)D1, A\mu_2v_2\omega_2(-)D2, A\mu_3v_3\omega_3(+)D3, \ldots, A\mu_{n-1}v_{n-1}\omega_{n-1}(-/+)Dn-1, A\mu_nv_n\omega_n(+/-)Dn$. If, for example, the units $A\mu v\omega$ are arranged in rows, then the units $D\mu$ are in the former case likewise arranged in a row on one (the right hand) side of the sample cuvette, in the latter case alternately in two rows on opposite sides of the sample cuvette. A translation of the planes is also conceivable. However, this will usually only be contemplated when the exciting light emitted by each of the units $A\mu v\omega$ is still perpendicularly incident on the outer surface of the sample cuvette. This will generally be the case with cuvettes having a rectangular cross section, but not with those having a round cross section.

These planes can also be rotated relative to one another. On projection along the longitudinal axis of the cuvette, thus, the optical axes belonging to two neighboring units $a\mu v\omega$ form an angle which is within the range from 0 to 360°. For example, when n is 2, 3, 4, 5 or 6 (and in the case of a regular, helical arrangement), the resulting angles between neighboring units $A\mu v\omega$ will be 180, 120, 90, 72 or 60°. For n equal to 3, 4, 5 or 6, complementary angles of 240, 270, 288 and 300° (or –120, –90, –72 or –60°) will imply a corresponding contrary helicity in the arrangement (not extant in the case of n equal 2, i.e., 180°). It may additionally be noted that, of course, here too the planes can be present not just in accordance with the sequence $A\mu_1v_1\omega_1(+)D1, A\mu_2v_2\omega_2(+)D2, A\mu_3v_3\omega_3(+)D3, \ldots, A\mu_nv_n\omega_n(+)Dn$ (equivalently thereto in the sequence $A\mu_1v_1\omega_1(-)D1, A\mu_2v_2\omega_2(-)D2, A\mu_3v_3\omega_3(-)D3, \ldots, A\mu_nv_n\omega_n(-)Dn$) but likewise for example in the sequence $A\mu_1v_1\omega_1(+)D1, A\mu_2v_2\omega_2(-)D2, A\mu_3v_3\omega_3(+)D3 \ldots, A\mu_{n-1}v_{n-1}\omega_{n-1}(-/+)Dn-1, A\mu_nv_n\omega_n(+/-)Dn$. For n equal 2 (180°) or 4 (90°) it is customary to use a cuvette having a rectangular cross section, while for n equal 3 (120°), 5 (72°) or 6 (60°) it would be customary to use (for n equal to 2 or 4 this is of course also possible) a cuvette having a circular cross section. The combination of excitation and detection of the n markers $M\mu$ can be carried out not only simultaneously but also in succession using the arrangements mentioned.

II.2) $A\mu_1v_1\omega_1/D, A\mu_1v_1\omega_1/D, \ldots, A\mu_{n-1}v_{n-1}\omega_{n-n}/D$ (the n markers $M\mu$ are each excited in the regions of overlap by the corresponding unit $A\mu v\omega$ and detected using a detection unit D, for example a multiwavelength detector.

a) The arrangement of the units $A\mu v\omega$ can be fashioned in accordance with the directions given under II.1). If the units $A\mu v\omega$ are arranged in a row (case $a_1$), the unit D can be fixedly mounted in the appropriate $\chi$-position, provided its radiation inlet window is sufficiently large or appropriate imaging optics are used. Otherwise (case $a_2$) a (translationally) readjustment into the appropriate position has to take place. In the case of the other arrangements of the units $A\mu v\omega$ (case $a_3$) a (translational and rotational) readjustment of the unit D into the corresponding $\chi$-positions has to take place. Thus, in case $a_1$, the combination of excitation and detection of the n markers $M\mu$ can take place not only simultaneously but also in succession, but only in succession in cases $a_2$ and $a_3$.

b) In principle an arrangement along the lines of b) under point I.3) is also possible; that is, the optical axis of unit D is parallel to the longitudinal axis of a cylindrical sample cuvette, and the units $A\mu v\omega$ are arranged in accordance with the directions given under II.1). However, this will result in different path lengths which have to be traveled through the sample by the fluorescent light reemitted by the respective markers $M\mu$ on its way to the unit D, and different solid angles at which the fluorescent light will fall on the unit D (or, to be more precise, its detection window). This can lead to inaccuracies in the detected intensities or has to be taken into account appropriately in the evaluations. In principle, however, in these arrangements, the combination of excitation and detection of the n markers $M\mu$ can take place not only simultaneously but also in succession.

II.3) $A\mu_1v_1\omega_1/D(1,2, \ldots, n-1,n), A\mu_2v_2\omega_2/D(1,2, \ldots, n-1,n), \ldots, A\mu_{n-1}v_{n-1}\omega_{n-1}/D(1,2 \ldots, n-1,n), A\mu_nv_n\omega_n/D(1,2, \ldots, n-1,n)$ (the n markers $M\mu$ are each excited in the regions of overlap $L\mu v\omega$ by the corresponding units $A\mu v\omega$ and detected).

a) The arrangements correspond essentially to those recited in a) under point II.2). Instead of one unit D (e.g., a multiwavelength detector), however, there is used a detection unit which for example (case $a_1$) contains interchangeable photodetectors and/or interchangeable optical filters (and optionally polarizers) $\delta_1\mu$. Furthermore, however, D can also contain a plurality of photodetectors $\delta_1\mu$ to which the respective reemitted fluorescent light is for example directed (case $a_2$) by means of optical fibers or optical fiber bundles. With a unit D corresponding to case $a_1$, the combination of excitation and detection of the n markers $M\mu$ can only take place in succession, since there will be a need to change the subunits $\delta_1\mu$ and optionally also for a (translational or translational and rotational) readjustment of the unit D. With a unit D corresponding to case $a_2$, the combination of excitation and detection of the n markers $M\mu$ can be carried out in succession and potentially also (given a suitable arrangement of the units $A\mu v\omega$ simultaneously if, for example through suitable optical facilities, a bundling (e.g., by means of an optical lens) of the fluorescent light simultaneously reemitted by the markers $M\mu$ onto the optical fibers or fiber bundles takes place.

b) The arrangements correspond essentially to those recited in b) under point II.2). Instead of one unit D (e.g., a multiwavelength detector), however, there is used again a detection unit which for example (case $a_1$) contains interchangeable photodetectors and/or interchangeable optical filters (and optionally polarizers) $\delta_1\mu$. Furthermore, however, D can also contain a plurality of photodetectors $\delta_1\mu$ to which the respective reemitted fluorescent light is for example directed (case $a_2$) by means of optical fibers or optical fiber bundles. With a unit D corresponding to case $a_1$, the combination of excitation and detection of the n markers $M\mu$ can only take place in succession. With a unit D corresponding to case $a_2$, the combination of excitation and detection of the n markers $M\mu$ can be carried out in succession and potentially also simultaneously. The observations in b) under II.2) concerning the different path lengths and solid angles of the fluorescent light reemitted by the markers $M\mu$ apply here too, of course.

II.4) $A\mu_1\nu_1\omega_1/A\mu_2\nu_2\omega_2/\ldots/A\mu_{n-1}\nu_{n-1}\omega_{n-1}/A\mu_n\nu_n\omega_n/D1/D2/\ldots/Dn-1/Dn$ (the n markers are simultaneously excited in the regions of overlap $L\mu\nu\omega$ by the corresponding units $A\mu\nu\omega$ and simultaneously detected by the units $D\mu$).

The simultaneous excitation and detection of the n markers can in principle be carried out using the arrangements and geometries described in part II.1), part II.2) in case $a_1$ of a), part II.2) in b), part II.3) in case $a_2$ of a) and part II.3) in case $a_2$ of b).

The arrangements and illustrative ways of constructing detection equipment in case I, i.e., in the case of excitation in the same sample volumes, are particularly useful for the chronologically consecutive excitation of the n markers $M\mu$.

The arrangements and illustrative ways of constructing detection equipment in case II, i.e., in the case of excitation in different sample volumes, are particularly suitable for the simultaneous excitation of all n markers $M\mu$. Of these arrangements and illustrative ways of constructing detection equipment, those are very particularly useful in which, in addition, the fluorescent light reemitted in each cane can be detected simultaneously at spatially different locations.

In general, the exciting light emitted by the units $A\mu\nu\omega$ can be irradiated into the sample in pulsed form or continuously, i.e., in continuous wave (CW) mode. Furthermore, the intensity of the exciting light from each unit $A\mu\nu\omega$ can be modulated with a frequency $f\mu\nu\omega$, so that this unit $A\mu\nu\omega$ will excite a similarly $f\mu\nu\omega$-intensity modulated fluorescent emission of the marker $M\mu$ which can be measured selectively by $D\mu$. It is customary to use for this modulating frequencies which differ from the frequency of the mains network (usually 50 Hz) and the integral and half-integral multiples of this frequency. In the case of the simultaneous excitation and detection of the fluorescent light reemitted by all markers $M\mu$, the different modulation frequencies $f\mu\nu\omega$ can be used to achieve an attribution of the fluorescent light to the respective marker $M\mu$ and also a better signal-to-noise ratio. Intensity-modulated fluorescent signals are customarily detected using the lock-in method.

A preferred embodiment of the inventive method for detecting markers in liquids which have been marked according to the method of the invention comprises the chronologically successive excitation of the n markers $M\mu$ by their corresponding units $A\mu\nu\omega$ in the same sample volume and the (chronologically successive) detection of the fluorescent light reemitted by each $M\mu$.

A further preferred embodiment of the inventive method for detecting markers in liquids which have been marked by the method of the invention comprises the simultaneous excitation of the n markers $M\mu$ by their corresponding units $A\mu\nu\omega$ in the same sample volume and the simultaneous or successive detection of the fluorescent light reemitted by each MA by means of a multiwavelength detector.

A further preferred embodiment of the inventive method for detecting markers in liquids which have been marked by the method of the invention comprises the simultaneous excitation of the n markers $M\mu$ by a polychromatic unit A in the same sample volume and the simultaneous or successive detection of the fluorescent light reemitted by each $M\mu$ by means of a multiwavelength detector.

A further preferred embodiment of the inventive method for detecting markers in liquids which have been marked by the method of the invention comprises the simultaneous excitation of the n markers $M\mu$ by respective units $A\mu\nu\omega$ intensity modulated with the frequency $f\mu\nu\omega$, in the same sample volume, and the simultaneous or successive detection of the respective intensity-modulated fluorescent light reemitted by $M\mu$.

A further preferred embodiment of the inventive method for detecting markers in liquids which have been marked by the method of the invention comprises the simultaneous excitation of the n markers $M\mu$ by the units $A\mu\nu\omega$ in different sample volumes in each case and the simultaneous or successive detection of the fluorescent light reemitted by $M\mu$ by means of the respective unit $D\mu$.

The units $A\mu\nu\omega$ preferably contain semiconductor lasers, semiconductor diodes or solid state lasers as light sources $\alpha_1\mu\nu\omega$. If all or some of the markers $M\mu$ are to be excited in their main absorption ranges $L\mu(x)$ (where x is, for example, 80, 90, 95 or 99), the light sources $\alpha_1\mu\nu\omega$ used in the units $A\mu\nu\omega$ are preferably semiconductor lasers, semiconductor diodes or solid state lasers which have a maximum emission in the region of the spectrum extending from $\lambda_{max}-100$ nm to $\lambda_{max}+20$ nm, where $\lambda_{max}$ is the wavelength of the absorption maximum of the respective markers $M\mu$. These maximum emissions are then generally within the corresponding main absorption ranges of the respective markers. Alternatively, however, it is also possible, as mentioned earlier, to adapt the main absorption ranges $L\mu(x)$ through suitable choice of x.

The photodetectors $\delta_1\mu$ in the units $D\mu$ are advantageously semiconductor detectors, especially silicon photodiodes or germanium photodiodes.

If all or some of the markers $M\mu$ are to be excited in their main absorption ranges $L\mu(x)$ (where x is, for example, 80, 90, 95 or 99), the optical filters used in the photodetectors $\delta_1\mu$ of the units $D\mu$ are preferably interference filters and/or cutoff filters having a shortwave transmission cutoff within the range from $\lambda_{max}$ to $\lambda_{max}+80$ nm, where $\lambda_{max}$ is the wavelength of the absorption maximum of the respective corresponding marker $M\mu$.

If desired, it is additionally also possible to use one or more NIR polarizers

The Examples hereinbelow illustrate the invention.

EXAMPLE 1

A mixture of 0.5 ppm of A ($PcH_2$-(3'-methylphenyloxy)$_4$) and 0.5 ppm a of B ($PcH_2$-(3'-methylpiperidino)$_4$) is dissolved in unleaded gasoline motor fuel (RON 95)—$PcH_2$ designating the phthalocyanine system where $Me^1$ (formula Ia) is two hydrogens and in each case one radical of the pairs $R^1$ and $R^4$, $R^5$ and $R^8$, $R^9$ and $R^{12}$ and also $R^{13}$ and $R^{16}$ in the formula Ia is hydrogen while the other is 3,'-methylphenyloxy or 3,'-methylpiperidino, respectively.

The absorption spectra of the markers A and B have the absorbances (in arbitrary units) recited in Table 1 at the wavelengths of 685 and 754 nm of the lasers used:

TABLE 1

| Laser | Absorbance A | Absorbance B |
|---|---|---|
| 685 nm | 1.3151 | 0.3137 |
| 754 nm | 0.0171 | 0.9954 |

It can be seen that excitation of A with a 685 nm laser will also excite B at the same time, albeit to a lesser extent.

On excitation of A with a 685 nm laser and of B with a 754 nm laser, the fluorescent signal from B is made up of a component which is due to excitation of B by the 685 nm laser and a component due to excitation of B by the 754 nm laser.

On using A and a (fraudulent) marker B', which has no region of overlap with A, and excitation of A with a 685 nm laser and of B' with a 754 nm laser, the fluorescent signal measured in the fluorescent region of B' would be smaller by the amount of the absent excitation of B' by the 685 nm laser.

Furthermore, to make doubly sure of the identity of the marker mixture of A and B (or, to be precise, of the marked liquid), it is possible, on the one hand, to determine the overall intensity of the fluorescent light passing through appropriate filters in the fluorescent regions of markers A and B, on simultaneous excitation, and, on the other, determine the individual intensities on excitation with the one laser and excitation with the other laser. These three measurements together form a (possible) unique fingerprint.

EXAMPLE 2

A mixture of 0.5 ppm of B ($PcH_2$-(3'-methylpiperidino)$_4$) and 0.5 ppm of C ($NcH_2$—($OC_4H_9$)$_8$) is dissolved in unleaded gasoline motor fuel (RON 95)—$NCH_2$ being the naphthalocyanine system where $Me^2$ (formula II) is two hydrogens and all the pairs $Y^1$ and $Y^2$, $Y^3$ and $Y^4$, $Y^5$ and $Y^6$ and also $Y^7$ and $Y^8$ in the formula II are $OC_4H_9$.

The absorption spectra of the markers B and C have the absorbances (in arbitrary units) recited in Table 2 at the wavelengths of 754 and 855 nm of the lasers used:

TABLE 1

| Laser | Absorbance B | Absorbance C |
|---|---|---|
| 754 nm | 0.9954 | 0.3824 |
| 855 nm | 0.0037 | 1.9860 |

It can be seen that excitation of B with a 754 nm laser will also excite C at the same time, albeit to a lesser extent.

On excitation of B with a 754 nm laser and of C with an 855 nm laser, the fluorescent signal from C is made up of a component which is due to excitation of C by the 754 nm laser and a component due to excitation of C by the 855 nm laser.

On using B and a (fraudulent) marker C', which has no region of overlap with B, and excitation of B with a 754 nm laser and of C' with an 855 nm laser, the fluorescent signal measured in the fluorescent region of C' would be smaller by the amount of the absent excitation of C' by the 754 nm laser.

Furthermore, to make doubly sure of the identity of the marker mixture of B and C, it is possible to determine the fluorescent signals in simultaneous and individual excitation, as carred out earlier, in Example 1.

EXAMPLE 3

A mixture of 0.5 ppm each of compounds A, B and C is dissolved in unleaded gasoline motor fuel (RON 95) and simultaneously excited with 3 lasers at 685, 754 and 855 nm. The resulting fluorescent light is filtered through three bandpass filters (transmitted wavelengths at 720, 790 and 860 nm) and detected with the aid of a silicon pin diode. The fluorescence intensities recited in Table 3 are obtained (arbitrary units):

TABLE 3

| Bandpass filter | Fluorescent signal |
|---|---|
| 720 nm | 2705 |
| 790 nm | 572 |
| 855 nm | 1589 |

EXAMPLE 4

A mixture of 2/9 (0.22) ppm of compound A, 8/9 (0.88) ppm of compound B and 8/9 (0.88) ppm of compound C is dissolved in unleaded gasoline motor fuel (RON 95) and simultaneously excited with 3 lasers at 685, 754 and 855 nm. The resulting fluorescent light is filtered through three bandpass filters (transmitted wavelengths at 720, 790 and 860 nm) and detected with the aid of a silicon pin diode. The fluorescence intensities recited in Table 4 are obtained (arbitrary units):

TABLE 4

| Bandpass filter | Fluorescent signal |
|---|---|
| 720 nm | 2340 |
| 790 nm | 950 |
| 855 nm | 2705 |

It is clear from Examples 3 and 4 that (given appropriate calibration) it is possible to distinguish different relative ratios of the markers and also different absolute amounts of the markers through the intensities of their fluorescent signals.

What is claimed is:

1. A method of marking liquids using at least two markers, wherein said markers absorb in the 600–1200 nm region of the spectrum and reemit fluorescent light and the absorption range of at least one marker overlaps with the absorption range of at least one other marker wherein said liquids do not contain biological material.

2. The method of claim 1, wherein markers are used whose respective maximum absorption wavelength is in the 600–1200 nm region of the spectrum.

3. The method of claim 1, wherein n markers are added, n being an integer from 2 to 10.

4. The method of claim 1, wherein n markers are added, n being an integer from 2 to 6.

5. The method of claim 1, wherein n markers are added, n being an integer from 2 to 4.

6. The method of claim 1, wherein markers added are compounds selected from the group consisting of metal-free and metal-containing phthalocyanines, metal-free and metal-containing naphthalocyanines, nickel-dithiolene complexes, aminium compounds of aromatic amines, methine dyes, squaric acid dyes and croconic acid dyes.

7. A method for detecting markers in hydrocarbons and hydrocarbon mixtures marked by the method of claim 1, which comprises using light sources which emit radiation in the absorption ranges of said markers and detecting the fluorescent light reemited by said markers, at least one of said light sources emitting radiation in the overlapping absorption range of at least one marker with that of at least one other marker and the number of light sources being less than or equal to the number of markers.

8. A method as claimed in claim 7, wherein said light sources are semiconductor lasers, semiconductor diodes or solid state lasers.

9. Hydrocarbons and hydrocarbon mixtures marked by the method of claim 1.

* * * * *

UNITED STATES PATENT AND TRADEMARK OFFICE
CERTIFICATE OF CORRECTION

PATENT NO. : 6,312,958 B1
DATED : November 6, 2001
INVENTOR(S) : Meyer et al.

It is certified that error appears in the above-identified patent and that said Letters Patent is hereby corrected as shown below:

<u>Title page,</u>
Item [30], Foreign Application Priority Data, should read:
-- [30]                Foreign Application Priority Data
Apr. 23, 1998    (DE) ...................................................198 18 176 --

Signed and Sealed this

Twenty-sixth Day of March, 2002

Attest:

JAMES E. ROGAN
*Attesting Officer*      *Director of the United States Patent and Trademark Office*